(12) United States Patent
Kadambi et al.

(10) Patent No.: US 10,527,562 B2
(45) Date of Patent: Jan. 7, 2020

(54) METHODS AND APPARATUS FOR X-RAY IMAGING FROM TEMPORAL MEASUREMENTS

(71) Applicants: Massachusetts Institute of Technology, Cambridge, MA (US); The General Hospital Corporation, Boston, MA (US)

(72) Inventors: Achuta Kadambi, Cambridge, MA (US); Ramesh Raskar, Cambridge, MA (US); Rajiv Gupta, Wayland, MA (US); Adam Pan, New Haven, CT (US)

(73) Assignees: Massachusetts Institute of Technology, Cambridge, MA (US); The General Hospital Corporation, Boston, MA (US)

(*) Notice: Subject to any disclaimer, the term of this patent is extended or adjusted under 35 U.S.C. 154(b) by 252 days.

(21) Appl. No.: 15/517,122

(22) PCT Filed: Oct. 29, 2015

(86) PCT No.: PCT/US2015/058169
§ 371 (c)(1),
(2) Date: Apr. 5, 2017

(87) PCT Pub. No.: WO2016/069959
PCT Pub. Date: May 6, 2016

(65) Prior Publication Data
US 2017/0248532 A1    Aug. 31, 2017

Related U.S. Application Data

(60) Provisional application No. 62/072,193, filed on Oct. 29, 2014.

(51) Int. Cl.
*A61B 6/10* (2006.01)
*G01N 23/083* (2018.01)
(Continued)

(52) U.S. Cl.
CPC ......... *G01N 23/083* (2013.01); *G01N 23/046* (2013.01); *G01T 1/248* (2013.01);
(Continued)

(58) Field of Classification Search
CPC .... G01N 23/04; G01N 23/046; G01N 23/083; G01N 2223/04; G01N 2223/419;
(Continued)

(56) References Cited

U.S. PATENT DOCUMENTS 6,649,914 B1   11/2003   Moorman et al.
6,728,335 B1   4/2004    Thomson et al.
(Continued)

OTHER PUBLICATIONS

Arques, M., et al., Dynamic X-ray direct conversion detector using a CdTe polycrystalline layer coupled to a CMOS readout chip; published in Nuclear Instruments and Methods in Physics Research Section A: Accelerators, Spectrometers, Detectors and Associated Equipment, vol. 633, Supplement 1, pp. S55-S58 (May 2011).
(Continued)

*Primary Examiner* — Jurie Yun
(74) *Attorney, Agent, or Firm* — Stephen R. Otis

(57) ABSTRACT

For each X-ray path through a tissue, numerous trials are conducted. In each trial, X-ray photons are emitted along the path until a Geiger-mode avalanche photodiode "clicks". A temporal average—i.e., the average amount of time elapsed before a "click" occurs—is calculated. This temporal average is, in turn, used to estimate a causal intensity of X-ray light that passes through the tissue along the path and reaches the diode. Based on the causal intensities for multiple paths, a computer generates computed tomography
(Continued)

(CT) images or 2D digital radiographic images. The causal intensities used to create the images are estimated from temporal statistics, and not from conventional measurements of intensity at a pixel. X-ray dosage needed for imaging is dramatically reduced as follows: a "click" of the photodiode triggers negative feedback that causes the system to halt irradiation of the tissue along a path, until the next trial begins.

20 Claims, 12 Drawing Sheets

(51) Int. Cl.
*G01N 23/046* (2018.01)
*G01T 1/24* (2006.01)
*G21K 1/04* (2006.01)
*H01J 35/06* (2006.01)
*H01J 35/14* (2006.01)

(52) U.S. Cl.
CPC ............ *G21K 1/043* (2013.01); *H01J 35/065* (2013.01); *H01J 35/14* (2013.01); *G01N 2223/04* (2013.01); *G01N 2223/1016* (2013.01); *G01N 2223/304* (2013.01); *G01N 2223/419* (2013.01)

(58) Field of Classification Search
CPC .......... H01J 35/06; H01J 35/065; H01J 35/14; G01T 1/24; G01T 1/248; G21K 1/04; G21K 1/043; A61B 6/06; A61B 6/542; A61B 6/10; A61B 6/4208; A61B 6/4241; A61B 6/54; G05F 1/575; H05G 1/56; H05G 1/30
USPC ......... 378/4, 16, 19, 62, 117, 145, 147, 160, 378/165, 901
See application file for complete search history.

(56) References Cited

U.S. PATENT DOCUMENTS

| | | |
|---|---|---|
| 7,403,589 B1 | 7/2008 | Short et al. |
| 2009/0022264 A1 | 1/2009 | Zhou et al. |
| 2009/0116720 A1 | 5/2009 | Ritman |
| 2011/0297833 A1 | 12/2011 | Takayama |
| 2012/0025074 A1 | 2/2012 | Barbi et al. |
| 2012/0177180 A1 | 7/2012 | Van Lemel et al. |
| 2012/0267746 A1 | 10/2012 | Sanfilippo et al. |
| 2013/0259344 A1 | 10/2013 | Petersilka et al. |

OTHER PUBLICATIONS

Birnbach, C., et al., Power Electron Tubes as an Enabling Technology for the Grid; published in http://www.cce.umn.edu/documents/CPE-Conferences/MIPSYCON-Papers/2012/PowerElectronTubesAsAnEnablingTechnologyForTheGrid.pdf (2012).
Bonard, J., et al., Carbon nanotube films as electron field emitters; published in Carbon, vol. 40, Issue 10, Aug. 2002, pp. 1715-1728 (2002).
Buller, G., et al., Single-photon generation and detection; published in Measurement Science and Technology, vol. 21, No. 1 (2010).
Itzler, M., et al., Geiger-mode avalanche photodiode focal plane arrays for three-dimensional imaging LADAR; published in Proc. SPIE 7808, Infrared Remote Sensing and Instrumentation XVIII, 78080C (Aug. 2010).
Kirmani, A., et al., First-Photon Imaging; published in Science, Jan. 3, 2014, vol. 343, Issue 6166, pp. 58-61 (2014).
Mazzillo, M., et al., Single-photon avalanche photodiodes with integrated quenching resistor; published in Nuclear Instruments and Methods in Physics Research Section A: Accelerators, Spectrometers, Detectors and Associated Equipment, vol. 591, Issue 2, pp. 367-373 (Jun. 2008).
Spinhirne, J., Micro pulse lidar; published in IEEE Transactions on Geoscience and Remote Sensing, vol. 31, Issue 1 (Jan. 1993).
Taguchi, K., et al., Vision 20/20: Single photon counting x-ray detectors in medical imaging; published in Medical Physics, vol. 40, Issue 10 (Oct. 2013).
Valastyan, I., Dual Slice Helical Computed Tomography, published at http://medim.sth.kth.se/hl2009/spiralCT-20090215.pdf (2009).

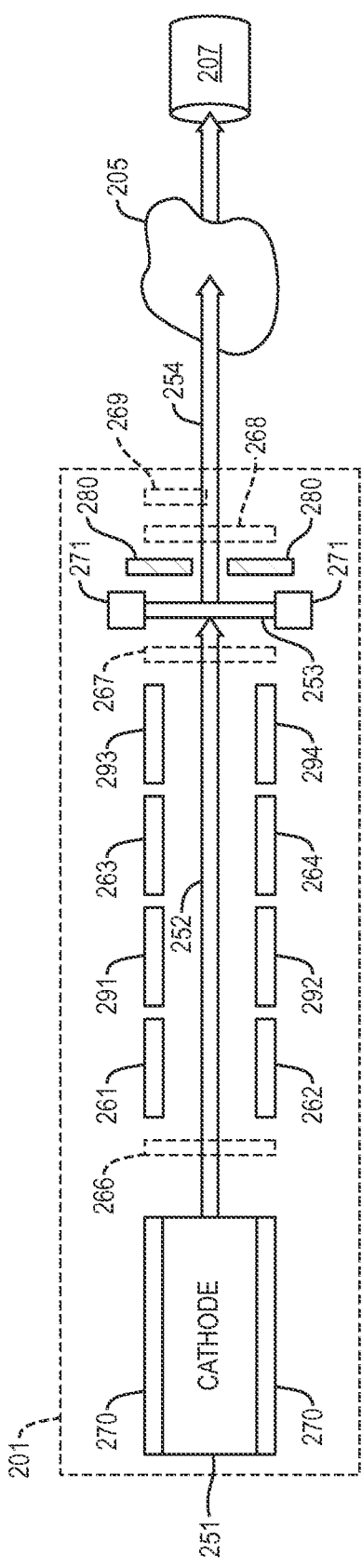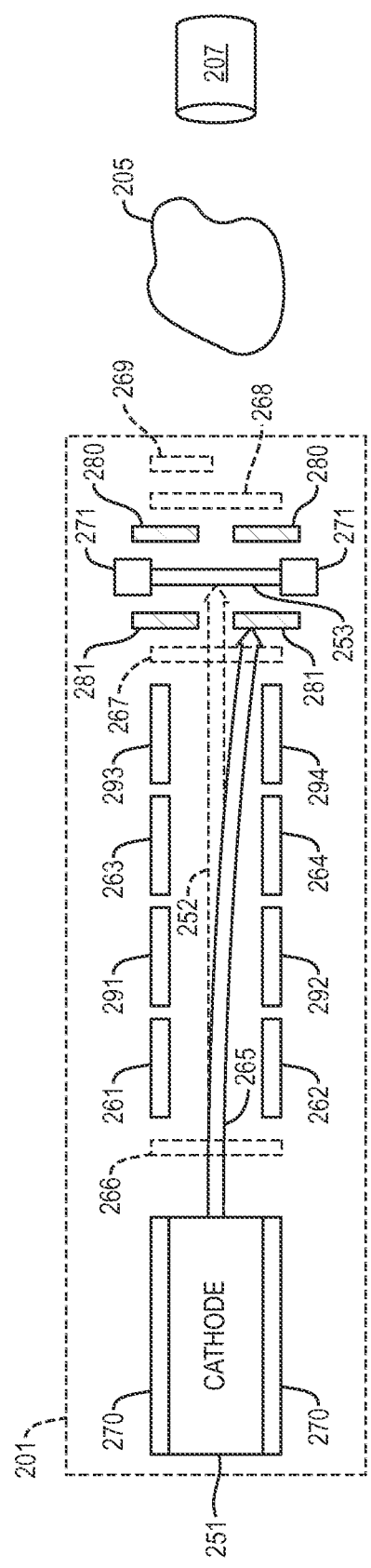
FIG. 2B
FIG. 2C

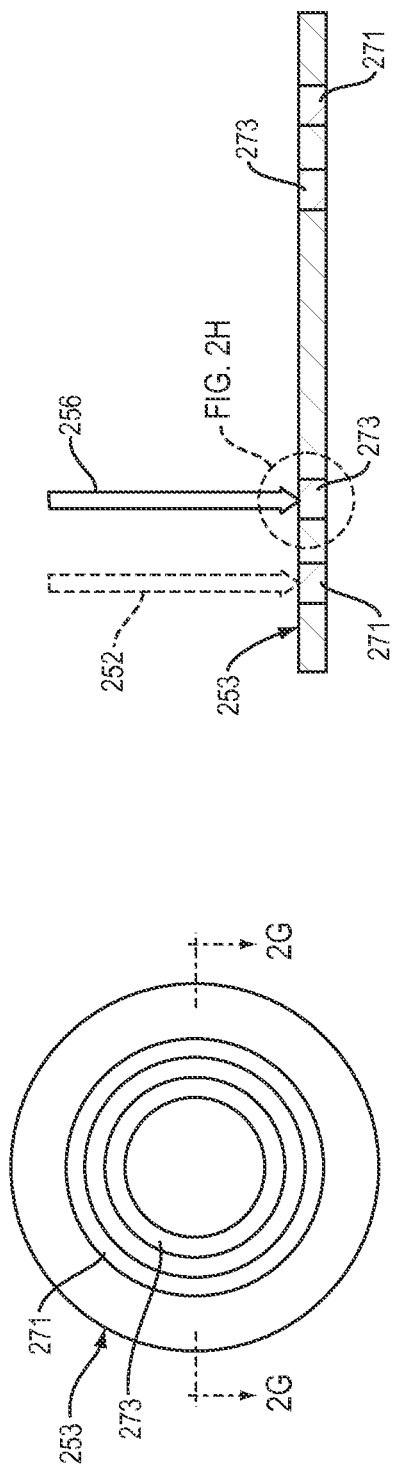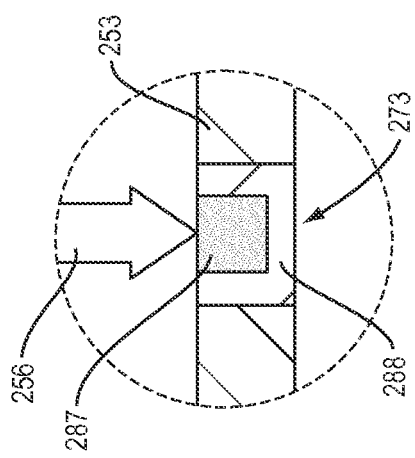

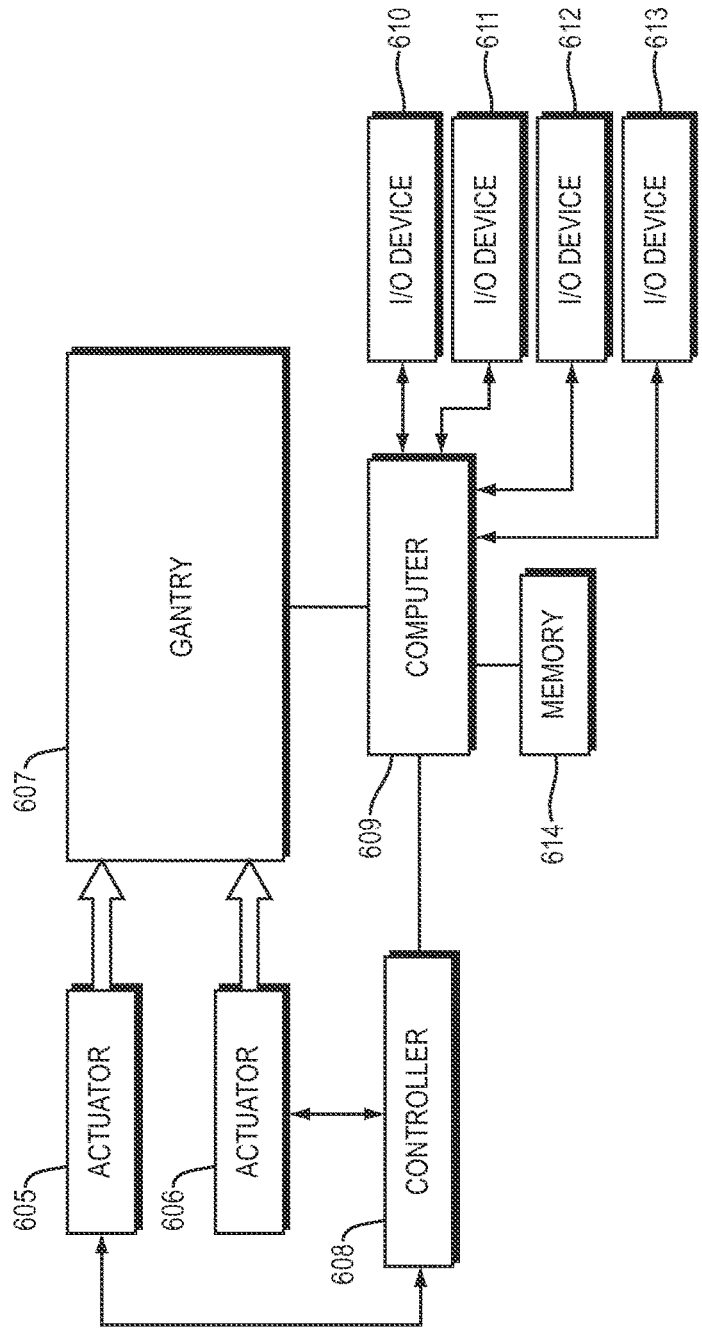

METHODS AND APPARATUS FOR X-RAY IMAGING FROM TEMPORAL MEASUREMENTS

RELATED APPLICATIONS

This application is a non-provisional of, and claims the priority of, U.S. Provisional Patent Application No. 62/071,293, filed Oct. 29, 2014, the entire disclosure of which is herein incorporated by reference.

FIELD OF TECHNOLOGY

The present invention relates generally to X-ray imaging, including computed tomography and digital radiography.

BACKGROUND

Conventional computed tomography (CT) exposes the patient to large doses of radiation, which create health risks, particularly if a patient undergoes many CT scans. The dosage in even a single CT procedure may be undesirable. For example, in some circumstances, a CT scan of the abdomen and pelvis (repeated with and without contrast material) exposes the patient to 20 mSv of radiation, which is the equivalent of 7 years of natural background radiation and is considered to create a moderate risk of cancer.

Even conventional radiographs (loosely called "X-rays") expose the patient to substantial doses of radiation, which if repeated over time, may have a cumulative effect that is harmful to health. For example, in some circumstances, a conventional radiograph of the spine exposes the patient to 1.5 mSv of radiation, which is the equivalent of 6 months of natural background radiation.

It is desirable to image tissue with X-rays, in a manner that sharply reduces the radiation dosage to the patient.

SUMMARY

In illustrative implementations of this invention, the dose of X-rays needed to acquire a computed tomography (CT) image or other X-ray image is dramatically reduced.

In order to understand how this invention sharply reduces dosage (e.g., in some cases, by more than a hundredfold), one must first understand the novel manner in which this invention acquires CT and other X-ray images.

It is easier to start with concrete examples first, before moving to a more general description.

In some embodiments of this invention, temporal measurements regarding the timing of "clicks" of a Geiger-mode avalanche photodiode—also called a single photon avalanche diode ("SPAD"). See paragraph 206 for a definition of "click". These temporal measurements are used to estimate attenuation of X-ray light that passes through a target.

In illustrative implementations, a sensor comprises one or more single-photon avalanche diodes (SPADs). Each SPAD is reversed-biased above its breakdown voltage, such that incident radiation on the SPAD above a threshold intensity (the "click threshold") triggers an avalanche current. In many cases, the click threshold is set at an intensity that is more than the intensity of one incident X-ray photon and less than 10 incident X-ray photons.

In illustrative implementations of this invention, the average amount of time that it takes a SPAD to "click" (undergo a current avalanche) is measured in repeated trials. This temporal average provides information regarding attenuation of X-ray light.

For X-ray photons traveling in tissue, the longer that it takes for a SPAD to "click", the more the tissue attenuates the X-ray light—and thus the lower the intensity of X-ray light that passes through the tissue.

For example, bone has a higher attenuation coefficient than muscle, and thus the probability that a given X-ray photon will pass through a distance of bone is less than the probability that a given X-ray photon will pass through the same distance of muscle. Thus, the average amount of time that it takes for a SPAD to click is greater for a train of X-ray photons traveling through a distance of bone than it is for the same train of photons traveling through the same distance of muscle.

For a given path (geometric straight line) that intersects a tissue, a given X-ray photon traveling along that path has a probability p of passing through the tissue and reaching the sensor, and a probability 1−p of being absorbed or scattered by the tissue and not reaching the sensor. The probability that a given X-ray photon will reach the sensor along the path—and thus the average amount of time that it takes for a SPAD to "click" due to X-ray photons traveling along the path—depend on the attenuation coefficient of the tissue along the path. Specifically, they depend on the line integral of the attenuation coefficient along the path.

In illustrative embodiments of this invention, numerous trials are conducted for a path of X-ray light that passes through tissue. Each trial comprises sending X-ray photons along the path, until a SPAD "clicks". In each trial, the amount of time that elapses before the SPAD clicks is measured. A computer calculates the average amount of time that elapses in these trials before the SPAD clicks.

This temporal average is used to calculate a causal intensity of X-ray light that passes through the tissue along the path. In some cases, the causal intensity is an estimate of the actual intensity of X-ray light that travels through the tissue along the path and reaches the SPAD.

(Without being limited by theory, the term "causal intensity" loosely suggests that one might, for some purposes, consider that this estimate of actual intensity as a causal variable in an inverse problem sense.)

This procedure is repeated for multiple paths through the tissue, in order to estimate a causal intensity for each of the paths.

In some cases, the causal intensities are used to generate a digital 2D X-ray image that is not a CT slice. In these cases, all of the paths "view" the tissue from the same angle—that is, all of the paths through the tissue are parallel.

In other cases, the causal intensities are used to generate computed tomography (CT) data regarding a volume, or slice of a volume, inside the tissue. In these cases, projection samples are taken along different angles through the tissue. The causal intensity for each path is used to calculate the attenuation of X-ray light along the path (specifically, to calculate a line integral of the attenuation coefficient along the path). The line integrals for the respective projections are, in turn, used to calculate the attenuation coefficient at discrete spatial points (voxels) within a 3D volume inside the tissue. This voxelized data is converted to Hounsfield units and used to generate CT images.

The causal intensities are estimates of relative intensity of X-ray radiation. The causal intensities are derived from the temporal averages, and not from measurements of actual intensity that are conventionally used to produce a CT image or 2D X-ray image. There is no need to measure actual intensity at each pixel in the conventional manner. Instead, in illustrative embodiments of this invention, an X-ray image or CT image is calculated from causal intensities that are estimated from the temporal averages.

In illustrative implementations of the invention, X-ray dosage during imaging is dramatically reduced as follows: a "click" of a SPAD triggers negative feedback that causes the X-ray imaging system to halt irradiation of the tissue along a path, at least temporarily.

For each trial along each path, the patient receives only (a) the very few X-ray photons that are needed to produce a "click" of the SPAD and (b) the few (if any) X-ray photons that impact the patient during the short time that it takes to halt X-ray radiation along the path.

In illustrative implementations, the negative feedback (triggered by the SPAD click) causes the radiation to temporarily halt along a path, until the next trial along the path begins. At the start of this next trial, the radiation begins again. If all trials along a given path have been completed, then the negative feedback halts radiation along the given path for the remainder of the imaging procedure.

In illustrative implementations, the method used to halt radiation may vary. For example, in some cases: (a) the X-ray cathode is a photocathode that emits electrons due to the photoelectric effect; and (b) X-ray radiation is halted by turning off the light source that illuminates the photocathode. In other cases: (a) the X-ray cathode is a field emission cathode that emits electrons by "cold" field emission in the presence of a strong electric field; and (b) X-ray radiation is halted by electrically disconnecting the field emission cathode from its power source, so that current stops flowing through the cathode. In yet other cases, the X-ray radiation is halted by interposing a mechanical shutter that (a) blocks electrons that would otherwise strike a region of an X-ray anode, or (b) blocks X-rays that are emitted by an X-ray anode. In some cases, the radiation is halted by deflecting an electron beam that would otherwise strike a region of an X-ray anode.

These halts in radiation dramatically reduce the total X-ray dose needed for imaging. For example, in some implementations of this invention, for each path, respectively: (a) less than 10 X-ray photons per trial travel on the path before a "click" of the SPAD; (b) less than 10 X-ray photons per trial travel on the path during the latency period between the "click" and the halt of radiation, and (c) less than 100 trials are conducted. This results in a much lower X-ray dosage than in conventional imaging.

This invention is not limited to imaging biological tissue, but instead may be employed for imaging any type of material. For example, this invention may be employed to produce X-ray images of a metallic object, such as to check for defects in a weld.

More generally:

In illustrative embodiments of this invention, temporal statistics regarding the timing of a detection event are used to estimate (a) intensity of X-ray radiation, (b) attenuation of X-rays by the object being imaged; and (c) radiodensity of the object being imaged. Numerous trials are performed. In each trial, an X-ray source emits X-ray photons along a path that intersects an object. In each of these trials, a sensor detects an event (a "detection event") that is stochastic and is due to at least some of photons passing through the object and reaching the sensor. Furthermore, in each of these trials, a timer measures a temporal duration that is stochastic and that depends, at least in part, on when the detection event occurs during the trial.

A computer calculates a temporal average that is an average of the temporal durations measured by the timer in the repeated trials.

Based on the temporal average, the computer calculates a causal intensity. The causal intensity is an estimate of intensity of X-ray light that passes through the object along the path and reaches the sensor.

In some embodiments, a 2D digital radiographic image is generated. In these cases, causal intensities are computed for many paths through the object being imaged. For each path, the causal intensity is estimated based on the temporal average for that path. Based on these causal intensities, a computer calculates the 2D digital radiographic image.

The causal intensities are estimated from the temporal averages and not from conventional measurements of actual intensity at each sensor pixel. Typically, the causal intensities are estimates of relative intensities, which are proportional to, but not the same as, the actual intensities. The system could be—and in some cases is—calibrated such that the causal intensities are estimates of actual intensity, rather than merely estimates of relative intensity. However, in many cases, there is little incentive to do so, since a digital X-ray image or CT image may be computed from relative intensities.

In other embodiments, a computed tomography (CT) image is generated. Here, too, causal intensities are computed for many X-ray paths through the object being imaged. Here, too, the causal intensities are estimated from the temporal averages and not from conventional measurements of actual intensity at each sensor pixel. The computer performs a CT reconstruction algorithm, such as filtered backprojection. Rather than using conventional measurements of actual intensity as inputs to the reconstruction program, however, the causal intensities are used as inputs to the reconstruction algorithm. For example: For each path through the object being imaged, a computer takes the causal intensity for that path as an input, and calculates a line integral of the attenuation coefficient along the path. The computer repeats this for many paths (projections) through the object being imaged, in order to calculate a set of line integrals of attenuation coefficients, one line integral for each path. Based on these line integrals, the computer calculates attenuation coefficients for a set of voxels in a volume of the object being imaged. The computer converts these attenuation coefficients into radiodensities expressed in Hounsfield units. The computer uses this Hounsfield data to generate a CT image.

When a detection event occurs, it triggers negative feedback that causes an X-ray source to halt, at least temporarily, emitting X-rays along the path.

The description of the present invention in the Summary and Abstract sections hereof is just a summary. It is intended only to give a general introduction to some illustrative implementations of this invention. It does not describe all of the details and variations of this invention. Likewise, the descriptions of this invention in the Field of Technology section is not limiting; instead it identifies, in a general, non-exclusive manner, a technology to which exemplary implementations of this invention generally relate. Likewise, the Title of this document does not limit the invention in any way; instead the Title is merely a general, non-exclusive way of referring to this invention. This invention may be implemented in many other ways.

BRIEF DESCRIPTION OF THE DRAWINGS

FIG. 2B and FIG. 2C each show an example of an X-ray source.

FIG. 2F shows an anode.

FIG. 2G shows a cross-section of an anode.

FIG. 2H shows a zoomed view of part of the cross-section of the anode.

FIGS. 6A, 6B, 6C and 6D show examples of a gantry trajectory. In FIGS. 6A, 6B, 6C and 6D, the trajectory is helical, linear, circular and semi-circular, respectively.

FIG. 6E shows hardware for actuating and controlling motion of a gantry.

Figure 1:
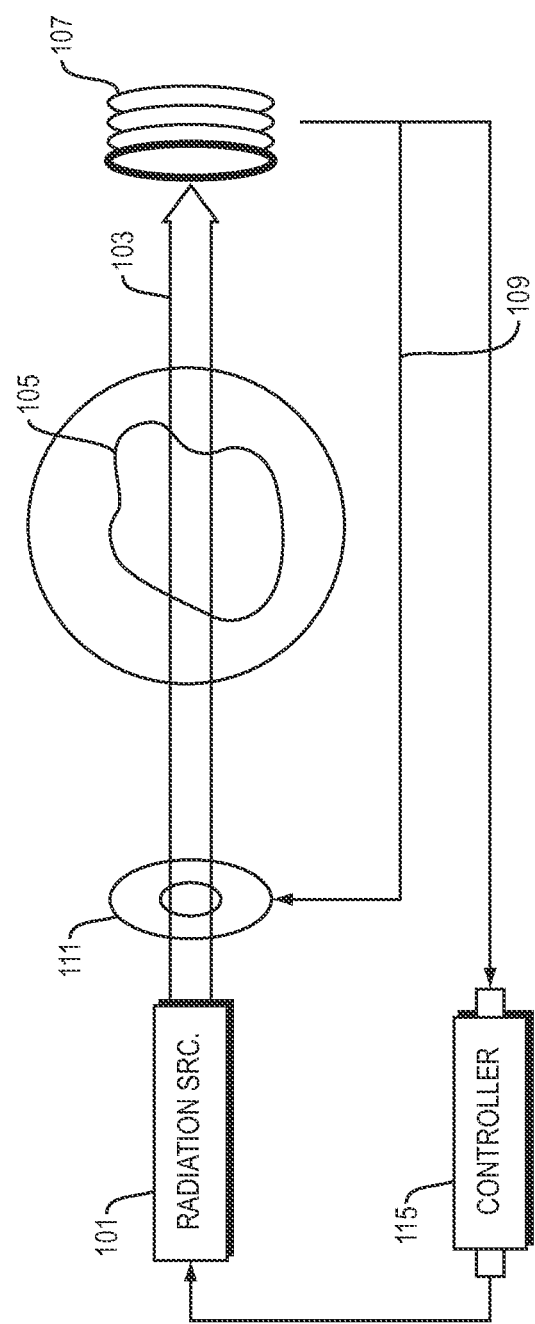
FIG. 1 is a conceptual diagram that shows an X-ray imaging system in which a "click" of a Geiger-mode avalanche photodiode triggers negative feedback that reduces the X-ray dose delivered to tissue during imaging.

The above Figures show some aspects of illustrative implementations of this invention. However, this invention may be implemented in many other ways.

DETAILED DESCRIPTION

In illustrative embodiments of this invention, temporal measurements regarding "clicks" of a single photon avalanche diode (SPAD) are taken. These temporal measurements are used to estimate attenuation of X-ray light that passes through a target and also to determine when to halt irradiation of the target.

This approach dramatically reduces the X-ray dose needed to acquire a CT or other X-ray image.

For example, in some cases, along a given trial along a given path, the patient receives only (a) the few X-ray photons that are needed to produce a "click" of the SPAD, and (b) the few (if any) X-ray photons that impact the patient during the short time that it takes to halt X-ray radiation along the path.

Model Description

The following 14 paragraphs illustrate principles of this invention, by describing a non-limiting example in which: (a) the X-ray radiation is monochromatic; and (b) the medium being imaged is homogeneous These conditions (a) and (b) are chosen to simplify the discussion. However, this invention is not limited to the model described in the following 14 paragraphs, but instead may be implemented in other ways, including scenarios in which (a) the X-ray radiation is multi-spectral; and (b) the material being imaged is not homogeneous.

Without loss of generality, assume that the medium is homogeneous and consider only a single projection. Then, for a monochromatic X-ray beam, Beer's law provides the following relation:

$$I/I_0 = \exp(-\mu L) \qquad \text{Equation 1}$$

where I is the measured intensity, $I_0$ is the input intensity, $\mu$ is the linear attenuation coefficient of the material, and L is the radiative path length. Assuming that the other variables are known, $\mu$ may be solved for. This process is repeated over different projections and the final image is formed by backprojection.

The standard model set forth in Equation 1 does not account for time varying signals at the source or detector. Consider a more general case where the X-ray source is modulated by a continuous-time pulse waveform, denoted by $p_t$. For simplicity, assume that $p_t$ directly models the number of photons that are emitted from the source. The discretized signal at the sensor plane takes the form of $$\tilde{p}_{[t]} = \alpha p_{t-z/c} \qquad \text{Equation 2}$$

where z is the propagation distance of light and c the speed of light. The relation between $\alpha$ and $\mu$ is of the form $$\alpha = \exp(-\mu L) \qquad \text{Equation 3}$$

Standard computed tomography may also be expressed within this framework by using DC signals, i.e., $p = I_0$ and $\tilde{p}_t = I$. Now consider the case where the detector is a single photon avalanche diode that clicks at some time $t^*$. Then, the total flux of photons incident on the surface, i.e., the dose, may be written as $$D = \gamma \eta \alpha \int_0^{t^*} p_{t-\tau}\, dt = \gamma \eta \alpha \int_{-\tau}^{t^*-\tau} p_t\, dt \qquad \text{Equation 4}$$

where $0 < \eta \le 1$ is the quantum efficiency of the detector, $\gamma \Sigma \mathbb{Z}^+$ is the click threshold of the detector, and $\tau$ is a general delay in the pulse (due to, for example, propagation distance z as described in Eq. 2). Through change-of-variable, $\tau$ appears in the limits of Equation 4.

The transmission probability of the medium may be estimated as $$\hat{p} = \left(\gamma \eta \alpha \int_{-\tau}^{t^*-\tau} p_t\, dt\right)^{-1} \qquad \text{Equation 5}$$

and the linear attenuation coefficient estimated as $$\hat{\mu} = \frac{1}{L} \ln \gamma \eta \alpha \int_{-\tau}^{t^*-\tau} p_t\, dt \qquad \text{Equation 6}$$

The method of estimating the attenuation coefficient in accordance with Equation 6 is sometimes called "transient CT" herein. Assuming a fixed quantum efficiency, transient CT reduces the X-ray dose over standard computed tomography when $\gamma < I$, with $\gamma$ and I defined above. Reason: For both modalities, the incident dose is written as $\tilde{r}\eta\gamma\alpha\int_{-\tau}^{t^*-\tau} p_t\, dt$. For transient CT, $\tilde{r}=1$; whereas for standard computed tomography $\tilde{r}=I$ and $\gamma=1$.

In illustrative implementations of this invention, transient CT is employed, and typical values for $\gamma$ range from 1 to 10, while typical values for I range from 10 to 1000. (In the preceding sentence, the click threshold $\gamma$ is expressed as an integer number of photon. For a monochromatic X-ray source, the number of photons is proportional to the watts measured at detector).

Thus, in some cases, transient CT may reduce dose by a factor of 1 to 1000 times, as compared to conventional CT.

An additional benefit of transient CT is that it delivers (to each spatial location in the tissue being imaged) an optimal X-ray dose—in the sense of the minimum dose needed for the sensor to receive one X-ray photon, given attenuation of the X-ray by the object—to each spatial location. In contrast, in conventional CT, I is heuristically chosen such that signal is received even at opaque regions; however, this overexposes the lucent regions.

The noise statistics of single photon imaging and conventional imaging differ. For instance, false positives from dark counts may occur in avalanche diodes (which can be mitigated by cooling or by increasing γ). Furthermore, although the dose is invariant to the pulse shape, the noise statistic will be different. The optimal pulse may be calculated by taking equation 6 and analyzing the propagation of errors.

A controller modulates the radiation source with waveform $p_t$. The time at which the photodiode clicked is sent to the controller, and a negative feedback loop turns off the exposure. This system may be implemented a number of ways, with either electronic or mechanical shuttering mechanisms or different types of detectors, for example, either avalanche diodes or photomultiplier tubes.

Consider a single sample of the discrete-time emitted pulse $p_{[t]}$. This corresponds to a discretized quanta of photons emitted from the source. Then, there is a probability, p, that the single photon is able to make it through the volume, and a set of measured outcomes based on the quantization of the detector. The scenario may be cast as a statistical problem, which follows for the case of one-bit quantization.

Define X: $\Omega \to \mathcal{R}$, where X~Bernoulli(p) and x is the realization of X. Specifically x is equal to 1 if the photon has been transmitted through the medium, else x=0. Define T: $\Omega \to \mathcal{R}$ with realization t; this random variable represents the number of trials that the experiment is repeated until x=1. The random variable T has a Geometric random distribution, with $\mathbb{E}[T]=1/p$, and $\mathrm{Var}[T]=(1-p)/p^2$.

For the application of measuring the linear attenuation coefficient—where p is not known a priori—it is desirable to estimate $\mathbb{E}[T]$ from the samples. An interesting question is how close this estimate is to the true expected value, and whether repeating the experiment would increase the accuracy of the estimate.

Let $T_1, \ldots, T_n$ be independent geometric random variables where $$Pr(T_i = j) = (1-p)^{j-1} p \text{ for all } j \in \mathbb{N}. \text{ Let } \Gamma := \sum_{i=1}^{n} T_i.$$

$$\text{Then for } \delta > 0, Pr(\Gamma \geq (1+\delta)\mathbb{E}(\Gamma)) \leq \exp\left(-\frac{\delta^2(n-1)}{2(1+\delta)}\right)$$

This is the Chernoff bound for geometric random variables.

For example, suppose it is desired to be 99 percent confident that the estimated expectation from samples is within 10 percent of the true expectation. Then, the Chernoff bound suggests that the single photon experiment should be repeated for at most n=1000 trials. This is a loose bound and in practice the number of trials for repetition may be far lower.

The preceding 14 paragraphs describe a non-limiting example of this invention. This invention may be implemented in many other ways.

Hardware, Generally

FIG. 1 is a conceptual diagram that shows an illustrative embodiment of this invention. Specifically, FIG. 1 is a conceptual diagram that shows an X-ray imaging system in which a "click" of a SPAD triggers negative feedback that reduces the X-ray dose delivered to tissue during imaging.

In FIG. 1, a controller 115 modulates the intensity of the X-ray radiation source 101 with waveform $p_t$. A measurement is taken, recording the time at which the SPAD clicks. This measurement is sent to controller 115. When the SPAD clicks, a negative feedback loop 109 turns off the exposure. This system shown in FIG. 1 may be implemented a number of ways, with either electronic or mechanical shuttering mechanisms and different types of detectors, for example, either SPADs or photomultiplier tubes.

For instance, this invention may be implemented as follows: Let $p_t$ takes the form of a pulse train, where each pulse contains, for instance, a single photon. Then once the single-photon detector clicks, two things happen: (i) the shutter is closed, and (ii) the number of pulses were fired is recorded. It is this latter value that is then backprojected to form the medical image. This invention may be implemented in many other ways, including having more photons within each pulse, using different pulse shapes, etc.

In FIG. 1, a radiation source 101 emits a beam 103 of X-ray photons that passes through tissue 105 and travels to a Geiger-mode avalanche diode, also known as single-photon avalanche diode (SPAD) 107. The SPAD is reversed-biased above its breakdown voltage, such that incident radiation on the SPAD above a threshold intensity (the "click threshold") triggers an avalanche current. In the example shown in FIG. 1, the click threshold is set at an intensity that is more than the intensity of one incident X-ray photon and less than 10 incident X-ray photons. The click threshold is set by adjusting the overvoltage applied to reverse bias the SPAD.

When a click of the SPAD occurs, the click triggers negative feedback 109 that halts irradiation of the tissue 105, at least temporarily. Item 111 in FIG. 1 is a symbolic representation of one or more components of the imaging system that cause this halt in radiation. This one or more components may be positioned anywhere in the X-ray imaging system, and are not limited to the spatial position of item 111 in FIG. 1. For example, the one or more components 111 that halt irradiation of the tissue may comprise at least one mechanical shutter that is interposed in the path of X-ray radiation emitted by the anode of the X-ray generator.

In FIG. 1, a controller 115 outputs signals that control the radiation source 101, and thereby control the X-ray radiation that radiation source 101 emits. For example, in some cases, the X-ray radiation comprises a signal, and the controller 115 controls the amplitude, timing, frequency, duty cycle or shape of the X-ray signal emitted by the radiation source 101.

Figure 2A:
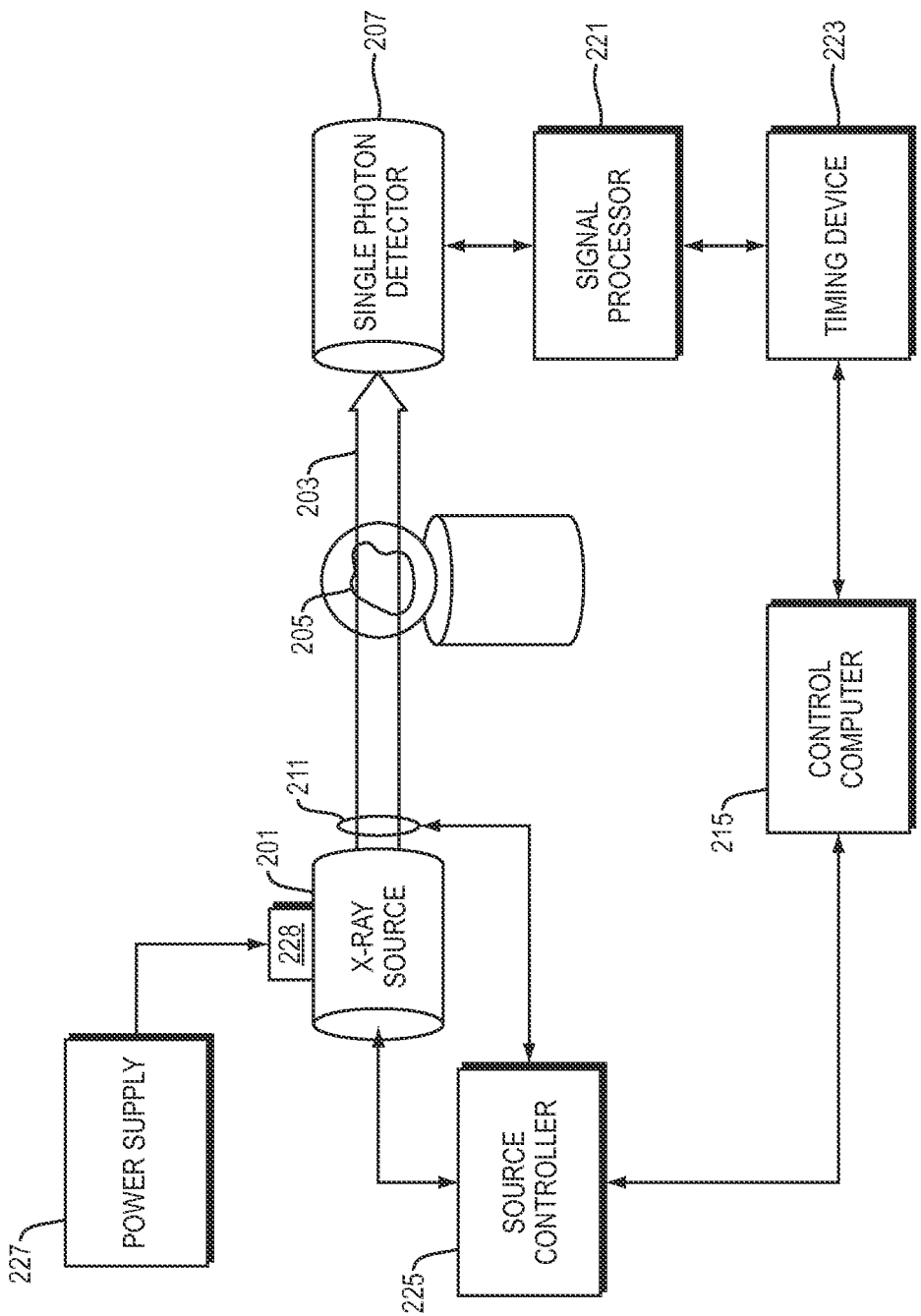
FIG. 2A shows hardware components of an imaging system.

FIG. 2A shows hardware components of an imaging system, in an illustrative embodiment of this invention. In FIG. 2A, an X-ray source 201 emits a beam 203 of X-ray photons that passes through tissue 205 and travels to a single-photon detector 207. The single photon detector comprises a single-photon avalanche diode (SPAD). When the click threshold is reached, the SPAD generates an avalanche current. A signal processor 221 amplifies the analog signal from the SPAD and converts it to a digital signal. An electronic timing device 223 receives the digital signal and measures the amount of time that it takes for the SPAD to click—e.g., the amount of time between the onset of a particular trial and the time it takes for the SPAD to click in that trial. (Numerous trials are conducted for each path through the tissue. Each trial consists of sending X-ray photons along the path, until the SPAD clicks.) The timing device 223 also generates signals to synchronize the X-ray source 201 and the single-photon detector 207. The timing device 223 comprises a microprocessor, integrated circuit, field programmable gate array (FPGA) or other computer, and in some cases includes other timing circuitry.

The timing device 223 notifies a control computer 215 that the SPAD has clicked. The control computer then outputs signals that cause a source controller 225 to halt irradiation of the tissue 205, at least temporarily. For example, the X-ray irradiation of the tissue along a given path may be halted until the beginning of the next trial for that path.

The source controller 225 comprises a microprocessor, integrated circuit, FPGA or other computer. The source controller controls the X-ray radiation emitted by the X-ray source 201, including when to start and when to halt X-ray radiation during a given trial. For example, in some cases: (a) an actuated mechanical shutter 211 is used to halt the radiation by blocking X-ray photons that are emitted by the anode of the X-ray source 201, and (b) the source controller 225 outputs signals that control an actuator that actuates movement of the shutter, causing the shutter to move into, or away from, a position in which the shutter blocks the X-ray photons.

For clarity of illustration, FIG. 2A shows a single SPAD. However, in practice, each X-ray detector in the X-ray imaging device may comprise an array of SPADs, and multiple X-ray detectors may be employed in a single X-ray imaging device.

X-Ray Source

FIG. 2B and FIG. 2C each show an example of an X-ray source, in an illustrative embodiment of this invention. In FIGS. 2B and 2C, X-ray source 201 includes a cathode 251 that emits electrons. A high-voltage electric field accelerates the electrons and focuses the path of the electrons such that the electrons impact a small region of an anode 253 at a high speed. The impact energy is so high that the anode 253 emits X-ray photons. Optionally, an annulus 280 shapes the beam 254 of X-ray photons that exits the anode 253, by restricting the range of angles of X-ray paths that pass through the annulus 280. Thus the annulus 280 at least partially collimates the X-ray beam. In FIG. 2B, X-ray beam 254 passes through object 205 and travels to X-ray sensor 207.

In many embodiments of this invention, the X-ray source 201 comprises a non-thermionic cathode—that is, the majority of the electrons emitted from the X-ray cathode are emitted by a process other than thermionic emission.

In some embodiments, the non-thermionic cathode is a photoelectric cathode that emits electrons when exposed to light (due to the photoelectric effect). For example, the photocathode may comprise magnesium or a magnesium alloy.

In some other embodiments, the non-thermionic cathode is a field emission cathode. The majority of the electrons emitted from the cathode are emitted by so-called "cold" electric field emission. In the field emission cathode, a strong electric field is applied to a substrate, causing the substrate to emit electrons. For example, the substrate may comprise carbon nanotubes, such as silicon carbide nanotubes.

In some implementations of this invention, the X-ray source 201 is thermionic—that is, the majority of the electrons emitted from the X-ray cathode are emitted by thermionic emission. In some cases, the thermionic cathode is directly heated (e.g., by resistive heating or induction heating of the cathode itself). In other cases, the thermionic cathode is indirectly heated by external heat sources 270. For example, external heat sources 270 may comprise resistive heating elements or induction heaters. However, external heat sources 270 would not typically be used for a non-thermionic cathode or for a directly heated, thermionic cathode.

More generally, any type of X-ray source may be used in this invention. For example, in some alternative embodiments of this invention, the X-ray source 201 comprises (a) a triboluminescent radiation source that directly produces small amounts of X-ray radiation through the breaking of chemical bonds through mechanical means); (b) an X-ray free electron laser; (c) a synchrotron; (d) a laser wakefield X-ray source; or (e) an X-ray source that uses electrons emitted by a self-magnetic pinch diode, rod pinch diode, or paraxial diode.

Halting Irradiation of Tissue after A "Click"

In illustrative implementations of this invention, a SPAD click triggers negative feedback that halts X-ray irradiation of tissue. It is desirable that this halt in radiation be effected very rapidly, in order to reduce the X-ray dose to the tissue.

In many embodiments of this invention, X-ray radiation is halted very rapidly after a SPAD click, by abruptly reducing electron flux from a non-thermionic cathode of an X-ray source.

An advantage of a non-thermionic cathode (such as a photocathode or field emission cathode) is that the electron flux from the non-thermionic cathode may be modulated at a very rapid rate. This, in turn, allows X-ray radiation to be turned off quickly after each SPAD click until the next trial, thereby reducing the radiation dose to the patient. Furthermore, rapid modulation of electron flux from the non-thermionic cathode facilitates rapid imaging and reduces motion artifacts (e.g., due to a patient moving during imaging).

In many embodiments in which a non-thermionic X-ray source is used, radiation may be modulated by changing inputs to the cathode, holding the anode at a fixed voltage. For example, in some cases, electron production is halted at the cathode side by: (a) turning off a light source that illuminates a photocathode, or (b) if a field emission cathode is used, electrically disconnecting the cathode from its power source, so that no current flows through the cathode.

Figure 2D:
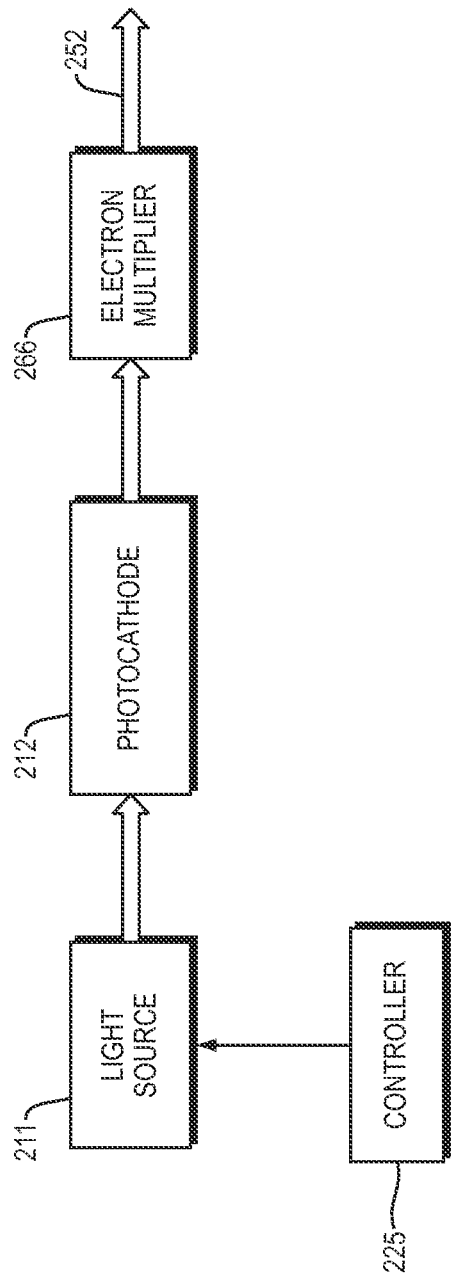
FIG. 2D shows a photocathode.

FIG. 2D shows an X-ray source that includes a photocathode. When the photocathode is exposed to light, it emits electrons.

Each trial comprises sending X-ray photons along a path until the SPAD for that path clicks. In the example shown in FIG. 2D: To start a trial, controller 225 outputs a signal that causes the light source 211 to turn on—i.e., emit light. This in turn causes the photocathode 212 to emit electrons, which in turn causes an electron beam to bombard the X-ray anode, which in turn causes the anode to emit X-rays. When the SPAD clicks, the controller 225 is notified. The controller 225 then outputs a signal that causes the light source 211 to turn off. This in turn causes the photocathode 212 to stop emitting electrons, which in turn causes the X-ray anode to stop emitting X-rays.

Figure 2E:
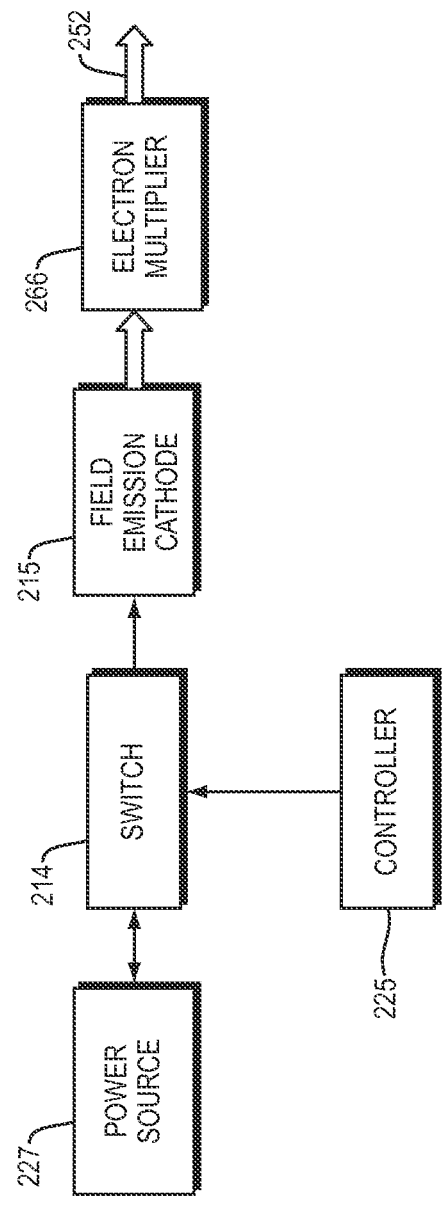
FIG. 2E shows a field emission cathode.

FIG. 2E shows an X-ray generator that includes a field emission cathode. While the field emission cathode 215 is exposed to a strong electric field (arising from the voltage difference between cathode 215 and anode of the X-ray generator), the cathode 215 emits electrons.

As noted above, each trial comprises sending X-ray photons along a path until the SPAD for that path clicks. In the example shown in FIG. 2E: To start a trial, controller 225 outputs a signal that causes a switch 214 to electrically connect the field emission cathode 215 to its power source 227, so that current flows through the cathode. This in turn causes the field emission cathode 215 to emit electrons, which in turn causes an electron beam to bombard the X-ray anode, which in turn causes the anode to emit X-rays. When the SPAD for the path clicks, the controller 225 is notified. The controller 225 then outputs a signal that causes switch 214 to turn off the field emission cathode (i.e., to electrically disconnect the cathode from its power source 227, so that no current flows through the cathode). This is in turn causes the field emission cathode 215 to stop emitting electrons, which in turn causes the X-ray anode to stop emitting X-rays.

In FIGS. 2D and 2E, the electrons emitted by the cathode (212, 215) to travel to an electron multiplier 266, which amplifies the electron yield. In some cases, the flux of electrons exiting the electron multiplier 266 is much greater (e.g., thousands or millions of times greater) than the flux of electrons entering the electron multiplier 266. The electrons exiting the electron multiplier comprise an electron beam 252 that travels to the X-ray anode 253. In some cases, the electron multiplier 264 comprises a micro-channel plate (MCP). For example, the MCP may comprise a chevron MCP (comprising two MCPS with channels rotated 180 degrees from each other) or a Z-stack MCP (comprising MCPs with channels aligned in a Z shape). In some cases, electron multiplier 266 comprises an electron multiplier tube.

In some embodiments, the non-thermionic cathode is a field emission cathode, which is modulated (turned on and off) at rates greater than 50 kHz, greater than 80 kHz, greater than 500 MHz or greater than 1 GHz. For example, in some embodiments, a carbon nanotube field emitter is modulated at a 100 kHz rate.

In contrast, the rate at which electron flux from a thermionic cathode may change is typically much slower. This is because the electron flux from a thermionic cathode depends on the temperature of the cathode. The rate at which the thermionic cathode cools or heats (and thus the rate at which the electron flux from the thermionic cathode changes) is much slower than the rate at which electron flux from a non-thermionic source may be modulated.

However, it is desirable, in some cases, to employ a thermionic cathode. In those cases, it is desirable to use other means (besides changing electron flux from the cathode) to halt X-ray irradiation of the tissue. These other means, described in more detail below, include mechanical shutters, or deflecting or slowing an electron beam. An advantage of these other means (of halting X-ray irradiation of tissue) is that they are well-suited for use with a thermionic cathode. A disadvantage, for at least mechanical shutters, is that the resulting modulation rate of the X-ray radiation is slower than is achievable by modulating electron flux from a non-thermionic cathode.

In some embodiments of this invention, the X-ray irradiation of tissue is halted by interposing a mechanical shutter 268 between the X-ray anode 203 and the tissue 205, in order to at least temporarily block X-rays emitted by the X-ray anode. See FIG. 2B. Shutter 268 comprise a material with a high atomic number (e.g., lead), and therefore has dense atomic structure with many electrons that absorb and scatter X-ray photons.

For example, in some cases, shutter 268 comprises a rapidly spinning chopper wheel with lead strips arranged in a radial pattern on the wheel. As the chopper wheel 268 spins, each lead strip in the chopper wheel periodically blocks the X-rays and each gap between the lead strips periodically allows the X-rays to pass. When the rotational speed of the chopper wheel is held constant, the X-ray radiation that exits the chopper wheel comprises a periodic rectangular-wave signal. The number of pulses of this rectangular wave before a SPAD click yields the attenuation coefficient. Once the SPAD clicks, the chopper wheel is stopped. Due to rotational inertia of the chopper wheel, a few extra pulses may be emitted into the tissue before the chopper wheel stops, slightly increasing the radiation dose to the tissue. However, the chopper wheel is not well-suited for producing an aperiodic, high modulation frequency, X-ray signal.

Alternatively, a mechanical shutter is interposed in the electron beam. Specifically, in some cases, the X-ray irradiation of tissue is halted by interposing a mechanical shutter 267 between the X-ray cathode 251 and the X-ray anode 253, in order to at least temporarily block electrons emitted by the X-ray cathode. See FIG. 2B.

Mechanical shutters 267 and 268 each include an actuator for actuating movement of the shutter, such as movement of the shutter into or out of a beam of electrons or of X-ray photons.

In some embodiments of this invention, X-ray irradiation of tissue is halted by deflecting an electron beam.

In some implementations of this invention, the X-ray source 201 includes electrode plates (e.g., 261, 262, 263, 264) or magnets (e.g., 291, 292, 293, 294) that are used to control the trajectory or speed of the electrons emitted by the X-ray cathode. See FIG. 2B. Among other things, the magnets or electrode plates may deflect, accelerate or decelerate the electrons in any direction.

For example, in some cases, electrode plates (e.g., 261, 262, 263, 264) are positioned alongside the electron beam. The voltage of the electrode plates may be adjusted in order to deflect electrons away from the anode 253 (or at least away from a focal region of the anode), such that the electrons impact a deflection target 281. In some cases, the deflection target 281 includes or is partially surrounded by shielding (e.g., lead shielding). The shielding blocks X-rays emitted by the deflection target from reaching the tissue 205.

Electrons emitted by the X-ray anode travel in a trajectory. In some implementations, the voltage of the electrode plates (261, 262, 263, 264) is changed after a SPAD clicks, causing the trajectory to deflect so that the trajectory intersects the deflection target 281.

In FIG. 2B, electron beam 252 is focused on a focal region of X-ray anode 253. In FIG. 2C, electron beam 252 has been deflected to a deflected trajectory 265, so that the electron beam impacts deflector target 281 and does not impact anode 253. In FIG. 2C, X-ray irradiation of tissue 205 has ceased and X-ray beam 254 has disappeared.

The shape and position of the deflection target 281 may vary, and is not limited to that shown in FIGS. 2B and 2C.

For example, in some cases, the deflection target 281 may be part of, or housed in, the anode 253. FIGS. 2F, 2G and 2H show an example, in which the deflection target is part of a rotating anode. Including the deflection target in the anode has practical advantages. Among other things: (a) the size of deflection is small (i.e., the distance from the focal region of the anode to the deflection target in the anode is small); (b) electrons that strike the deflection target are captured by the anode; and (c) the cooling apparatus for the anode is also used to cool the deflection target. For example, in some cases, the anode is cooled in part by using an annular focal track and rotating the anode rapidly (so that different parts of the focal track are struck by electrons at different times). An annular deflection target located on the rotating anode may be cooled in the same manner. Furthermore, a cooling apparatus that cools the anode may easily cool a deflection target that is housed in the anode (which is advantageous, because heat is generated when electrons impact the deflection target).

In FIGS. 2F, 2G and 2H, an X-ray anode 253 includes a focal track 271 and a deflection target 273. Both the focal track 271 and deflection target 273 are annular in shape. The focal track 271 comprises a tungsten or molybdenum alloy. During X-ray irradiation of the tissue, electron beam 252 strikes the focal track 271 and the focal track emits X-ray photons.

In FIGS. 2F, 2G and 2H, when the electron beam is deflected (e.g., by electrode plates, as described above), the deflected electron beam has a deflected trajectory 256. Electrons traveling on this trajectory strike the deflection target 273 instead of the focal track 271. The deflection target 273 includes conductive material 287 and X-ray shielding 288, such as lead, barium sulfite or graded-Z shielding. The X-ray shielding 288 blocks X-rays emitted by region 287 when region 287 is struck by the material. Thus, while the electron beam is deflected from focal track 271 to deflection target 273, the X-ray radiation of the tissue ceases.

Alternatively, in some cases, magnets (e.g., 291, 292, 293, 294 in FIG. 2B) are positioned alongside the electron beam. The magnets may comprise magnetic coils. The magnetic fields created by the magnets may be adjusted in order to deflect electrons. For example, the magnets may deflect the electrons away from the anode 253, such that the electrons impact the deflection target 281, as shown in FIG. 2C. Or the magnets may deflect the electrons away from the focal track 271 of anode 253 to a deflection target located on the same anode 253, as shown in FIGS. 2F, 2G and 2H.

In some implementations of this invention, X-ray irradiation of tissue is halted by slowing or stopping the electrons (with or without deflecting them), such that the electrons impact the X-ray anode at a reduced speed or not at all. Because the electrons are traveling slower, they strike the anode (if at all) with a lower energy. As a result, the anode does not emit X-rays (or emits much fewer X-rays) during the halt. For example, in some cases, the decrease in electron speed is achieved by reducing the voltage difference between the X-ray anode and X-ray cathode. The voltage of the X-ray cathode, X-ray anode or both may be changed in order to reduce or eliminate this voltage difference. Similarly, an electric field generated by electrode plates (e.g., 261, 262, 263, 264) may be used to slow or stop the electrons, either alone or in conjunction with reducing the voltage difference between the X-ray anode and X-ray cathode. Likewise, an electric field generated by magnets (e.g., 291, 292, 293, 294) alongside the electron beam may be used to slow or stop the electrons, either alone or in conjunction with reducing the voltage difference between the X-ray anode and X-ray cathode.

An advantage of deflecting or slowing the electron beam is that X-ray radiation can be stopped abruptly, without changing the electron flux from the X-ray cathode. Thus, deflecting or slowing the electron beam may be used to halt X-ray radiation, even when the X-ray generator has a conventional thermionic cathode. Furthermore, deflecting or slowing the electrons allows the X-ray radiation to be started and stopped rapidly during each trial, and thus facilitates rapid image acquisition and reduces motion artifacts.

In illustrative embodiments of this invention, the halt of radiation is usually temporary. After X-ray radiation along a given path is halted, the radiation remains halted until the next trial along that path occurs. If the SPAD click occurs during the last trial for a given path, then X-ray radiation along the path halts for the remainder of the imaging procedure.

(In addition, of course, the X-ray imaging device as a whole may be turned on and off in a conventional manner. Also, in some cases where a thermionic cathode is used, the thermionic cathode may be turned on and off in a conventional manner.)

The pairs of electrode plates or magnets used for deflecting or slowing electrons may be positioned in different configurations. In some cases, as shown in FIGS. 2B and 2C, pairs are positioned at particular locations (displacements) along the length of the electron beam 252, but there is only one pair at each such location. FIGS. 2B and 2C show an example of this configuration. In FIGS. 2B and 2C, electrons tend to be deflected primarily up and down.

Figure 2I:
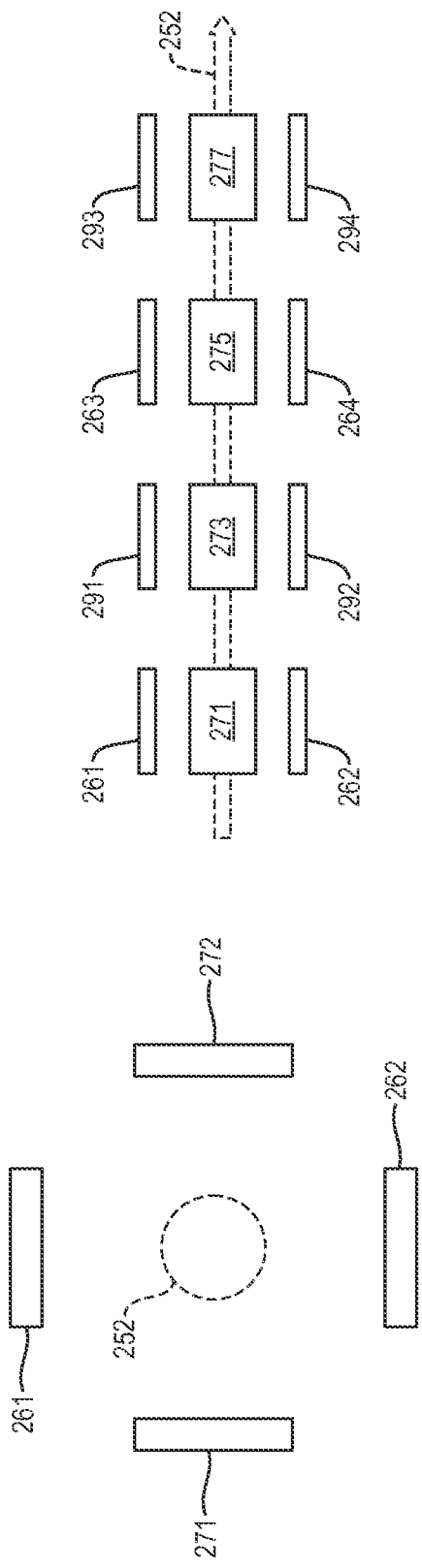
FIG. 2I shows two pairs of electrode plates positioned alongside an electron beam.
Figure 2J:
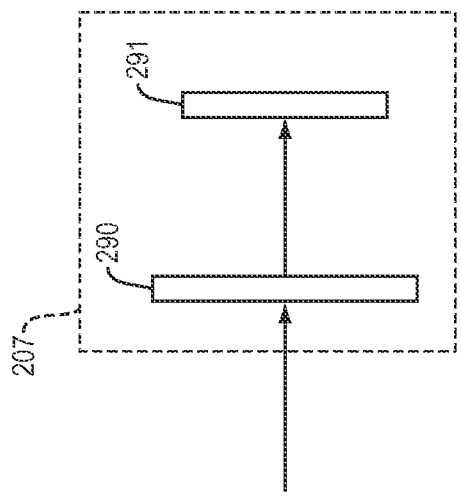
FIG. 2J shows electrode plates and magnets positioned alongside an electron beam.
Figure 2K:
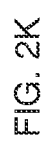
FIG. 2K shows a single-photon detector that includes a scintillator panel.

Alternatively: (a) pairs are positioned at particular locations (displacements) along the length of the electron beam 252, and (b) two pairs of electrode plates or magnets are positioned at each such location. FIGS. 2I and 2J show an example of this configuration. In FIGS. 2I and 2J, electrons may be controllably deflected up and down, and side-to-side.

In FIG. 2I, two pairs of electrode plates are arranged at the same displacement along the length of electron beam 252. The first pair 261, 262 are above and below electron beam 252; the second pair 271, 272 are on the right and left sides, respectively, of electron beam 252.

In FIG. 2J, at total of eight electrode plates and eight magnets are positioned along the length of electron beam 252. A first set of electrode plates is located at one location (displacement) along the length of electron beam 252, and a second set of electrode plates is located at another position along the beam. The first set of plates consists of plates 261, 262, 271 and 272. (Electrode plate 272 is not visible in FIG. 2J because it is occluded by plate 271.) The second set of plates consists of plates 263, 264, 275 and a plate that is occluded by plate 275. Similarly, a first set of four magnets is located at one position along the length of the electron beam 252, and a second set of four magnets is located at another position along the beam. The first set of magnets consists of magnets 291, 292, 273 and a magnet that is occluded by magnet 271. The second set of magnets consists of magnets 293, 294, 277 and a magnet that is occluded by magnet 277. In this paragraph, occluded means occluded from the vantage point of a person of viewing FIG. 2J and thus not visible in FIG. 2J.

Other Hardware Components

In illustrative implementations, one or more power sources 227 provide AC or DC power. One or more power regulators 228 regulate voltage or current provided to components of the X-ray source (including anode, cathode, and any magnets, electrode plates, deflection target, electric motors, other actuators, and cooling systems) and to other components of the X-ray imaging system (including X-ray sensors, other sensors, computers, controllers, timers, electric motors, other actuators, wireless communication devices, and signal processors). The one or more power regulators comprise, in some cases, a combination of one or more of the following components: voltage regulators, current regulators, vacuum tube devices, thyristors, electron tubes, cold cathode electron tubes, bi-directional cold cathode electron tubes, switches, power inverters, rectifiers, and transformers. The one or more power regulators are electrically connected to each component of the X-ray imaging system by switchable connections that may be opened or closed.

In the examples shown in FIGS. 2B and 2C, the X-ray source 201 includes one or more electron multipliers 264 (e.g., MCPs or electon multiplier tubes) that increase the electron yield.

In many embodiments of this invention, the X-ray anode 253 includes a focal region comprising tungsten, tungsten-rhenium or a molybdenum alloy, such as molybdenum-vanadium or molybdenum-niobium. For example, a molybdenum alloy may be desirable for mammography.

In some cases, the X-ray anode 253 comprises, or is part of, a rotating disk. Rotation of the disk causes the focal region of the anode to change over the course of each rotation, and thus helps prevent overheating. For example, in some cases: (a) the anode comprises, or is part of, a rotating molybdenum-alloy disk with a tungsten focal track 271, and (b) the disk is attached via a rod to an electric motor, which actuates rotation of the disk 253. See FIGS. 2F and 2G.

In some embodiments, a cooling system 271 cools the anode 253 to prevent over-heating of the focal region of the anode. For example, the cooling system may circulate a fluid such as water or oil, in order to cool the anode.

In FIGS. 2A, 2B, and 2C, a single-photon detector 207 measures incident X-ray photons that have passed through an object being imaged, such as tissue 205.

In illustrative embodiments of this invention, the single-photon detector comprises either: (a) a single photon avalanche diode (SPAD); (b) a superconducting nanowire single-photon detector (SNSPD); (c) a photomultiplier tube (PMT); or (d) a CdTe direct detection sensor.

In many embodiments of this invention, the single-photon detector 207 is a single photon avalanche diode (SPAD). The SPAD uses the photoelectric effect, in the first stage, to convert an optical signal into an electronic signal. When applied with a reverse bias voltage, electron-hole pairs are accelerated with sufficient energy to displace additional electrons from the silicon substrate. A regular avalanche photodiode (APD) has a reverse-bias voltage that is set below the breakdown voltage. In contrast, the reverse bias voltage of a SPAD is set higher than the breakdown voltage. A SPAD provides much higher gain than an ordinary APD, and is designed to detect as little as one photon. illustrative embodiments of this invention, the click threshold of the SPAD is set at higher than the energy of one X-ray photon, in order to mitigate dark current noise. For example, in some use scenarios, the click threshold is set to the level less than the energy of 20 photons and more than the energy of one photon. In some embodiments of this invention, the single-photon detector 207 is a SPAD that comprises an InGaAs photodiode.

In many embodiments, the single-photon detector 207 includes a scintillator panel 290 that converts X-rays into detectable wavelengths (e.g. 375-1000 nm). The scintillator panel is robust to X-rays. FIG. 2I shows a single-photon detector 207 that includes a scintillator panel 290 and one or more SPADs 291. The scintillator panel 290 emits visible light photons when bombarded by X-rays, and the SPADs 291 detect the visible light photons.

In some embodiments of this invention, the single-photon detector 207 comprises an X-ray direct conversion detector using a CdTe polycrystalline layer coupled to a readout chip. However, direct detection photon counting devices (such as a CdTe sensor) are less robust to X-rays, since radiation will directly bombard the chip.

In some embodiments of this invention, a single-photon detector 207 detects when an X-ray photon arrives, but cannot measure the energy level of the incident X-ray photon.

In other embodiments, the single-photon detector 207 discriminates among multiple energy levels (e.g. 10-15 kEv or 15-20 kEv) of an incident X-ray photon. The total statistics may be used to compute an overall transmission probability at all energy levels/wavelengths.

In illustrative implementations, a controller (e.g., 115, 225) controls the flux emitted by the X-ray radiation source (e.g., 101, 201).

X-Ray Waveform

In many cases, the X-ray flux emitted by the X-ray anode—while the flux is ongoing during a trial and is not temporarily halted—comprises a rectangular waveform.

The duty cycle of the rectangular waveform may vary, depending on the particular implementation of this invention. There is a tradeoff, in setting the duty cycle of the rectangular waveform. A higher duty cycle reduces image acquisition time (and thus reduces motion artifacts), but also requires a faster temporal resolution by the single-photon detector. A lower duty cycle allows the single-photon detector to have a lower temporal resolution (an advantage), but tends to lengthen image acquisition time and thus to increase motion artifacts (disadvantages). In illustrative embodiments, the duty cycle ranges from less than 1% up to 100%. In many cases, the duty cycle is or approaches 100%, in order to facilitate rapid image acquisition. This requires high temporal resolution of the single-photon detector.

In many embodiments of this invention, a packet of photons is sent in each pulse of the duty cycle. It is desirable to know how many photons, on average, are sent in each pulse. (Reason: in order to estimate the attenuation coefficient of tissue from the attenuated X-ray radiation exiting the tissue, it is helpful to know how many X-ray photons enter the tissue).

It is difficult to know how many photons, on average, are in each pulse, because the X-ray source 201 itself has a noise fluctuation (mostly Poissonian). To solve this difficulty, in some cases, an additional detector 269 measures the un-attenuated X-ray intensity. For example, in some cases, additional detector 269 comprises a single-photon detector. In the example shown in FIG. 2D, the additional detector 269 is positioned in a portion of the X-ray beam 254 and measures the X-ray beam intensity before the beam is attenuated by the tissue (or other object) 205 being imaged.

In some embodiments of this invention, during each trial, the X-ray generator emits an X-ray pulse waveform. When the SPAD clicks, this causes the X-ray generator to stop (at least temporarily) emitting this pulse waveform.

In some embodiments, the duty cycle of the X-ray pulse waveform starts low in each trial and increases over time during the trial (until the SPAD clicks). For example, the duty cycle increases in some cases as follows. If a SPAD click is not observed in an initial set of pulses (e.g., the first 1,000 pulses), it may be desirable to increase the duty cycle and thus the energy of subsequent pulses. Such a pulse shape (with a higher duty cycle) would result in an imaging system that has fine resolvability of lucent tissues (i.e., those that would click in the first thousand pulses), but coarser resolution of denser, attenuating tissues.

Temporal Measurements with Multiple X-Ray Detectors:

In illustrative embodiments of this invention, temporal measurements are taken. These temporal measurements measure the amount of time that it takes, during a trial along a given X-ray path, for a "click" of a SPAD to occur.

These temporal measurements may be taken for multiple X-ray paths concurrently. Multiple X-ray detectors and one or more X-ray generators are used for taking these measurements. These detectors and generator(s) may be arranged in a variety of different spatial configurations.

Figures 3A, 3B:
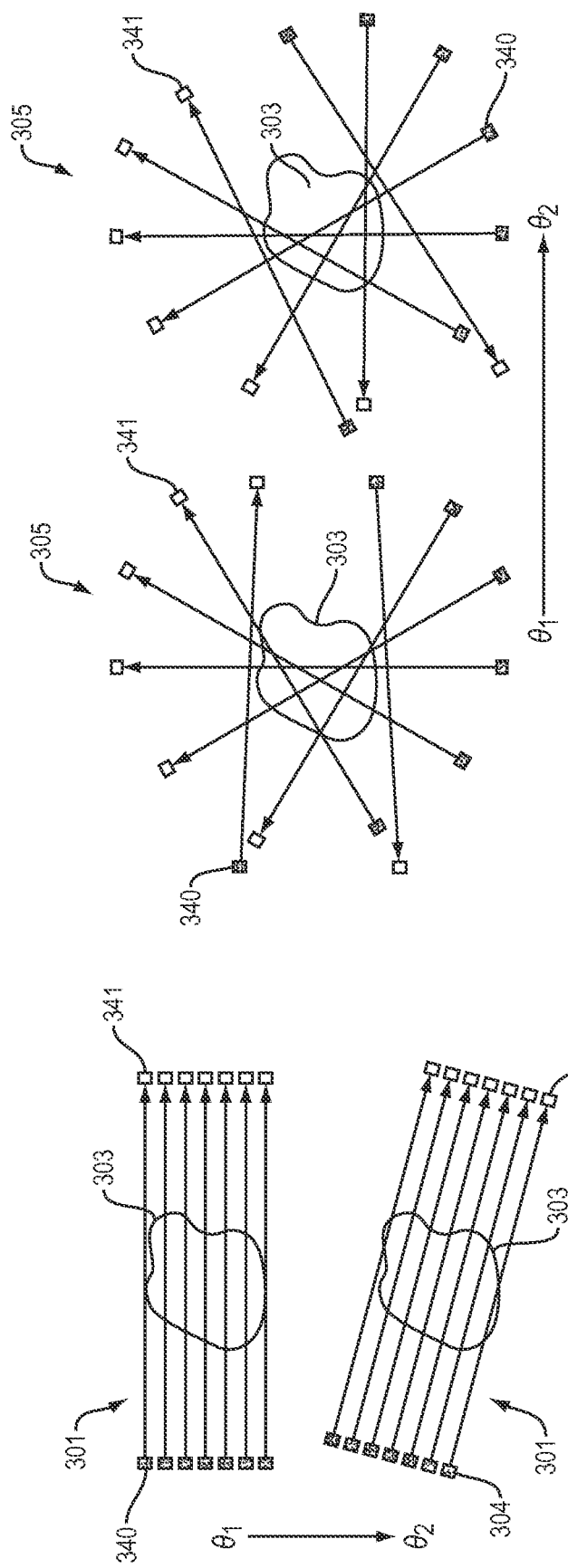
FIG. 3A shows tight packing of source-detector pairs.
FIG. 3B shows angular-spaced packing of source-detector pairs.

FIG. 3A shows an example of tight packing, in an illustrative embodiment of this invention. In FIG. 3A, a set 301 of source-detector pairs are positioned such that their X-ray beams are parallel to each other and tightly packed (close to each other). The X-ray beams intersect an object 303 being X-rayed. Each source-detector pair comprises an X-ray emitter (e.g., 340) and a SPAD (e.g. 341).

In FIG. 3A, in order to gather samples along different angular projections for CT imaging, the set 301 of source-detector pairs is rotated from angle $\theta_1$ to angle $\theta_2$. However, throughout this rotation, the X-ray beams remain parallel to each other and their position relative to each other does not change.

In FIGS. 3A and 3B, each arrow between an X-ray emitter and X-ray detector represents a "pencil" X-ray beam (i.e., a collimated X-ray beam, rather than a diverging X-ray beam). The direction of the arrow indicates the direction of travel of the photons in the pencil X-ray beam.

In FIG. 3A, the sources and detectors are closely spaced together and—within each angular snapshot—all pencil beams are at the same orientation. This approach is referred to as tight packing due to the close spacing of pencil beam detectors and sources. The tight packing refers to the general concept. For example, it may be implemented by rasterizing a single source-detector pair across different offsets, or by using multiple source-detector pairs at different offsets.

FIG. 3B shows an example of angular-spaced packing, in an illustrative embodiment of this invention. In FIG. 3B, a set 305 of source-detector pairs are arranged such that they are further apart and their X-ray beams intersect the object 303 at different angles at any given time.

In FIG. 3B, in order to gather samples along different angular projections for CT imaging, the set 305 of source-detector pairs is rotated from angle $\theta_1$ to angle $\theta_2$. However, throughout this rotation, the position of the X-ray beams relative to each other does not change.

In FIG. 3B, the orientation of each source-detector pair is different within each angular snapshot.

There are at least two advantages to the angular packing technique, in some cases. First, if the sources or detectors are bulky, the tight packing approach may not be feasible. Second, angular packing decreases cross-talk—both electronic and optical—between source-detector pairs.

In illustrative embodiments of this invention, it is desirable to minimize cross-talk between source/detector pairs. Cross-talk between source-detector pairs tends to distort the shutoff time t* (i.e., the time at which the "click" occurs), and thus tends to increase the X-ray dosage to the patient during imaging. One way to mitigate this cross-talk is to use the "pencil" (i.e., collimated) X-ray beams. However, it may not always be practical or desirable to use pencil beams. This invention is not limited to pencil beams. For example, in FIG. 3B, the angular spaced packing has a radial spacing of 30 degrees. Thus, each source-detector pair in FIG. 3B may alternatively be implemented using small fan beams and an array of sensors (e.g. SPAD sensors) at the detector. In that case, each beam diverges by less than 30 degrees, in order to mitigate cross-talk.

Figure 4:
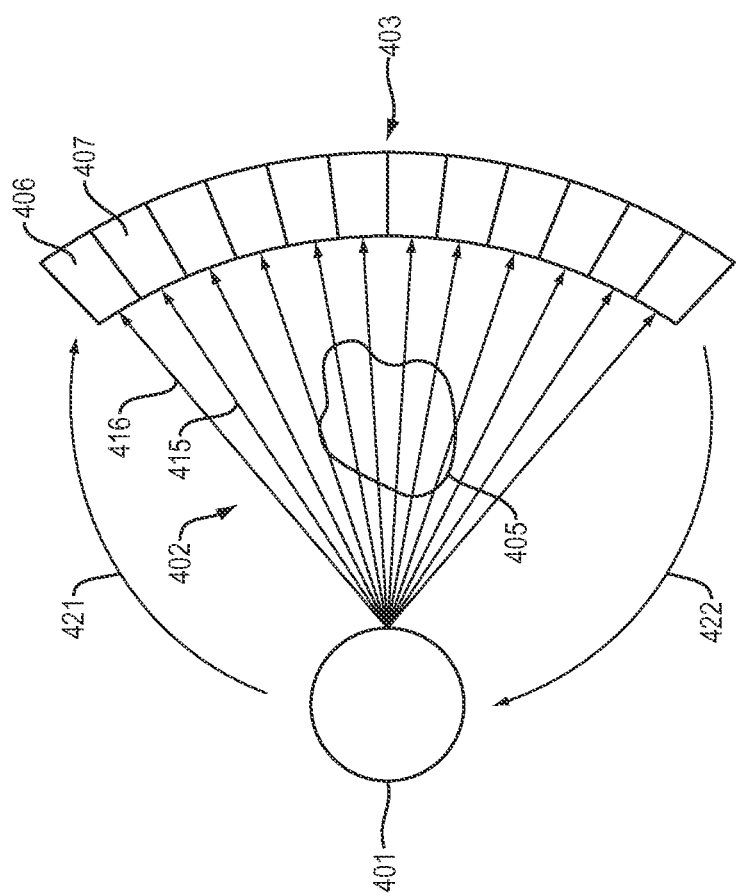
FIG. 4 shows a "fan" configuration of source-detectors.

FIG. 4 shows a "fan" configuration of X-ray source-detectors, in an illustrative embodiment of this invention. In FIG. 4, an X-ray source 401 emits a fan-shaped X-ray beam. An array 403 of SPADs (e.g., SPAD 406 and SPAD 407) detects the fan-shaped X-ray beam 402 that intersects an object 405. Preferably, the array 403 is positioned along a curve, such that the SPADs in array 403 are equidistant from X-ray source 401.

Alternatively, in FIG. 4, the X-ray source 401 emits a cone-shaped X-ray beam. In this "cone" alternative, array 403 is preferably in the general shape of a 3D curve, such that each SPAD in the array is equidistant from the source 401. In this "cone" alternative, FIG. 4 shows a 2D slice of the cone-shaped beam and the sensor array.

In some cases, the X-ray source 401 and array 403 of SPADs are attached to a gantry. The gantry rotates in a circular or spiral trajectory. Arrows 421 and 422 represent this rotation. The other arrows in FIG. 4 represent paths of X-ray light that are part of the overall fan or cone beam.

Figure 5A:
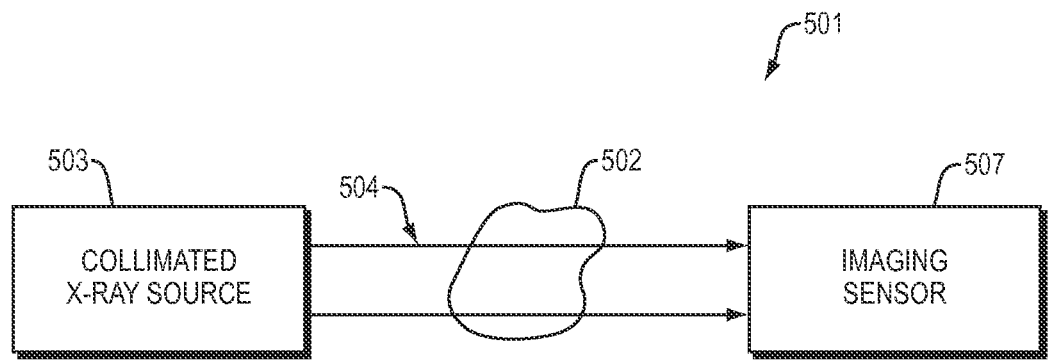
FIG. 5A shows a single source-detector pair.

FIG. 5A shows a single X-ray source-detector pair, in an illustrative embodiment of this invention. In FIG. 5A, an X-ray source 503 emits a pencil (i.e., collimated) beam 504 of X-ray light. An imaging sensor 507 detects the beam. In FIG. 5A each arrow represents a path of X-ray light that is part of the collimated beam. The direction of the arrow represents the direction in which the X-ray photons travel.

Figure 5B:
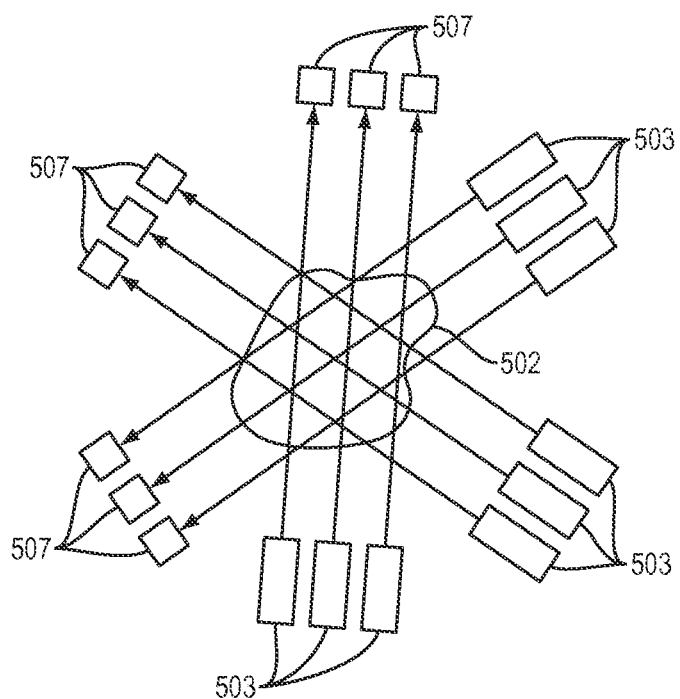
FIG. 5B shows multiple sets of source-detector pairs.

FIG. 5B shows three sets of source-detector pairs, in an illustrative embodiment of this invention. Each source-detector pair comprises an X-ray source 503 that emits a pencil beam of X-rays and an imaging sensor 407 that detects the beam.

Each set of source-detectors pairs comprises a set of tight-packed pairs that have parallel beams. The three sets of source-detector pairs are positioned such that the angle at which the beams intersect object 502 varies from set to set.

In FIG. 5B, each arrow represents a pencil beam. The direction of the arrow represents the direction in which the X-ray photons travel.

The timing of when to shut off radiation may vary, depending on the source-detector groups that are employed.

In some cases, each X-ray source is paired with only one X-ray detector. The logic for the timing is simple: When a "click" is detected by the X-ray detector in a pair, negative feedback causes the X-ray source in the same pair to stop emitting X-rays.

In other cases, a source-detector group comprises a single X-ray source and multiple X-ray detectors. Such a group may be used, for example, if the source emits a fan or cone beam. For such cases, at least two different approaches to timing may be used. In the first approach, once each of the detectors in the group has "clicked" during a trial, the entire fan or cone beam is turned off. In the second approach, when a detector in the group "clicks" during a trial, the portion of the fan or cone that is directed toward that detector is turned off, but the portion of the fan or cone that is directed at detectors that have not yet clicked during the trial continue to receive X-ray radiation. Thus, in this second approach, different regions of a beam of emitted X-rays are turned off at different times.

In some implementations of this invention, multiple X-ray detectors and at least one X-ray source are attached to a gantry. The gantry (and the detectors and source(s) attached to the gantry) are translated relative to the object being imaged. The translation may be along any route, including a linear, circular or helical route, depending on the particular implementation.

FIGS. 6A, 6B, 6C and 6D show examples of the trajectory of a gantry, in an illustrative embodiment of this invention. FIG. 6A shows a helical trajectory 601. FIG. 6B shows a linear trajectory 602. FIG. 6C shows a circular trajectory 603. FIG. 6D shows a semi-circular trajectory 604.

FIG. 6E shows hardware for actuating and controlling motion of a gantry, in an illustrative embodiment of this invention. Actuators 605, 606 actuate motion of the gantry 607 along a trajectory, such as a helical, linear, circular or semi-circular trajectory. In FIG. 6E, multiple X-ray detectors and source(s) are attached to the gantry, and thus travel in the same trajectory as the gantry. A controller 608 controls the actuators, and thus controls the motion of the gantry. The controller 608 comprises a microcontroller, integrated circuit, FGPA or other computer. In turn, another computer 609 controls the controller 608. Computer 608 stores data in, and accesses data from, an electronic memory device 614. Computer 614 interfaces with multiple input/output (I/O) devices 610, 611, 612, 613. For example, in some implementations, I/O devices 610, 611, 612, 613 comprise a keyboard, mouse, touch electronic display screen, and microphone, respectively.

Alternatively, in some embodiments of this invention, the X-ray detectors and X-ray source(s) remain stationary relative to the object being imaged, throughout the imaging process.

Temporal Measurements

In illustrative embodiments of this invention, attenuation of X-rays is estimated from temporal measurements. In some cases, the temporal measurements measure how long it takes for a detection event (e.g., a "click" of a SPAD) to occur. In some cases, the detection event occurs when the sensor measures an intensity that indicates that a threshold number of X-ray photons have struck the sensor. This threshold number of X-ray photons is typically less than 100 photons, or less than 50 photons, or less than 40 photons, or less than 30 photons, or less than 20 photons, or less than 10 photons.

A temporal duration that ends when the detection event occurs is the simplest case. More generally, in illustrative embodiments of this invention, the temporal duration being measured in each trial is a duration that is stochastic and depends, at least in part, on when the detection event occurs. For example, in some cases, the temporal duration being measured may end a short time after the detection event.

In many implementations of this invention: (a) the sensor is a single-photon avalanche diode (SPAD); (b) the detection event occurs when intensity measured by the SPAD reaches the click threshold of the SPAD, and (c) the detection event comprises a current avalanche. The detection event is sometimes called a "click".

(Despite its name, a so-called "click" does not itself create a humanly-audible noise. Nor, in illustrative implementations, does it cause any sensor or other apparatus to produce noise. The word "click" is used, by way of a loose analogy to a Geiger counter that makes audible clicks.)

The greater the attenuation along a given X-ray path through an object being imaged, the longer it takes for a detection event to occur.

Numerous trials are conducted for each path through the tissue. Typically, the number of trials is less than 1,000, or less than 500, or less than 400, or less than 300, or less than 200, or less than 100, or less than 50, or less than 40, or less than 30, or less than 20.

In each trial, X-ray photons travel on the path until the sensor "clicks". A computer calculates the average amount of time elapsed before a "click" occurs for a given X-ray path through the tissue.

Based on these temporal measurements (regarding amount of time before a click), a computer calculates the average amount of time elapsed in a trial, before the "click" for that trial occurs.

The average amount of time elapsed (before a "click" occurs in trials for a given path) is used to estimate a causal intensity of X-ray light that reaches the sensor along a given path. The estimated causal intensity is an estimated relative intensity. The causal intensities for multiple paths are used to derive computed tomography (CT) data regarding a volume, or slice of a volume, inside the tissue, or to produce a 2D X-ray image that is not a CT slice.

Thus, in illustrative embodiments of this invention, a transmissive image is calculated from temporal statistics. Photon counts are converted into temporal statistics. The temporal statistics are explicitly converted into attenuation:

Whether or not a given X-ray photon will pass through the tissue being imaged is a Bernoulli random variable.

The amount of time T that it takes for a "click" to occur (due to X-ray photons propagating along a given path) is also a random variable.

In illustrative embodiments of this invention, this amount of time T is either a gamma random variable, an Erlang random variable, a negative binomial variable, or a geometric random variable.

In illustrative embodiments of this invention, if the amount of time T is treated as a continuous-time random variable, then the statistical distribution of T is a gamma distribution. The sensor measurements are samples of the gamma distribution with shape and scale parameters corresponding to the intensity at detector and threshold of the detector. When the threshold is one single photon, the gamma distribution is equivalent to an Erlang distribution with its parameter set to the intensity at detector.

In illustrative embodiments of this invention, if the amount of time T is treated as a discrete time random variable, then the statistical distribution of T is a negative binomial distribution. The parameters of the negative binomial distribution are defined by the average number of photons hitting the detector with each packet (i.e. the photon survival probability multiplied by the average number of photons sent) and the photon threshold. In the case where the threshold is a single photon, the negative binomial distribution becomes a geometric distribution.

CT Imaging and 2D X-Ray Imaging

In illustrative embodiments of this invention, temporal measurements are taken for each path in a set of X-ray light paths. These temporal measurements record the time that elapses before a SPAD "clicks" due to X-rays traveling along the path. Numerous trials are run for each path. The amount of time that it takes for the "click" to occur is measured in each trial. For each path, a computer: (a) takes these temporal measurements from the repeated trials as input; and (b) based on these temporal measurements, calculates an average amount of time elapsed before the "click" occurs.

This temporal statistic (average amount of time elapsed) is used to calculate a causal intensity. The causal intensity is an estimated relative intensity of the X-ray light that has passed through the tissue along the path and reached the SPAD.

In some cases, the causal intensities are used to generate a digital 2D X-ray image that is not a CT slice.

In other cases, the causal intensities are used to generate computed tomography (CT) images. In these cases, projection samples are taken along different angles through the tissue. The causal intensity for each path is used to calculate the attenuation of X-ray light along the path (specifically, to calculate a line integral of the attenuation coefficient along the path). The line integrals for the respective projections are, in turn, used to calculate the attenuation coefficient at voxels within a 3D volume inside the tissue. The attenuation coefficients are converted to Hounsfield units, and a CT image is generated.

The causal intensities are estimates of relative intensity of X-ray radiation. The causal intensities are derived from the temporal averages, and not from measurements of actual intensity that are conventionally used to produce a CT image or 2D X-ray image.

In some cases, a lookup table is created, such as by precomputing inverse gamma distributions for expected flux or count values. Later, the precomputed lookup table is accessed to speed up computations.

In illustrative embodiments of this invention, any conventional algorithm used for CT reconstruction may be employed. However, in illustrative embodiments of this invention, estimated causal intensities derived from temporal averages are used as inputs for the reconstruction algorithm, rather than conventionally measured actual intensities. Rather than using a measured actual X-ray intensity at a pixel of a sensor as input to the reconstruction algorithm (the conventional approach), an estimated causal intensity derived from a temporal statistic regarding timing of "clicks" is used an input to the reconstruction algorithm. For example, the temporal statistic may be the expected (i.e., average) value of the amount of time until a "click" occurs in a trial.

Thus, in illustrative embodiments of this invention, any CT reconstruction algorithm may be employed, using estimated causal intensity as an input—rather than using actual intensity measured in the conventional manner as an input. For example, the reconstruction algorithm that is employed (using the causal intensities as an input) may be any of the following types of algorithms: filtered backprojection, 2D filtered backprojection, simple backprojection, iterative, ART (algebraic reconstruction technique), SIRT (simultaneous image reconstruction technique), Least squares or Likelihood (Poisson), Feldkamp Davis Kress, TPR (tilted plane approximation), 2D Approximate Algorithm, SSR (single-slice rebinning), ASSR (advanced single-slice rebinning), AMPR (adaptive multiplane reconstruction), interpolation, 360-Degree Linear Interpolation Algorithm, 180 Degree Linear Interpolation Algorithm, longitudinal interpolation by z-filtering, fan-beam reconstruction, cone-beam reconstruction, total variation minimizing compressive reconstruction, OSCaR (open source cone-beam CT reconstruction tool), Statistical Reconstruction Algorithm for Polyenergetic X-ray CT, and Simplified Statistical Image Reconstruction Algorithm for Polyenergetic X-ray CT.

In illustrative embodiments of this invention, the reconstruction algorithm takes the causal intensities as an input and outputs the linear attenuation coefficients of the object at each voxel. A computer then converts the attenuation coefficients into Hounsfield units for purposes of clinical CT imaging.

More generally, in illustrative embodiments of this invention, any reconstruction algorithm (or combination of algorithms) that takes the temporal measurements as an input and that outputs the attenuation coefficients for a set of voxels, may be employed. Alternatively, any reconstruction algorithm (or combination of algorithms) that takes the temporal measurements as an input and that outputs the Hounsfield units for a set of voxels, may be employed.

Flowcharts

Figure 7:
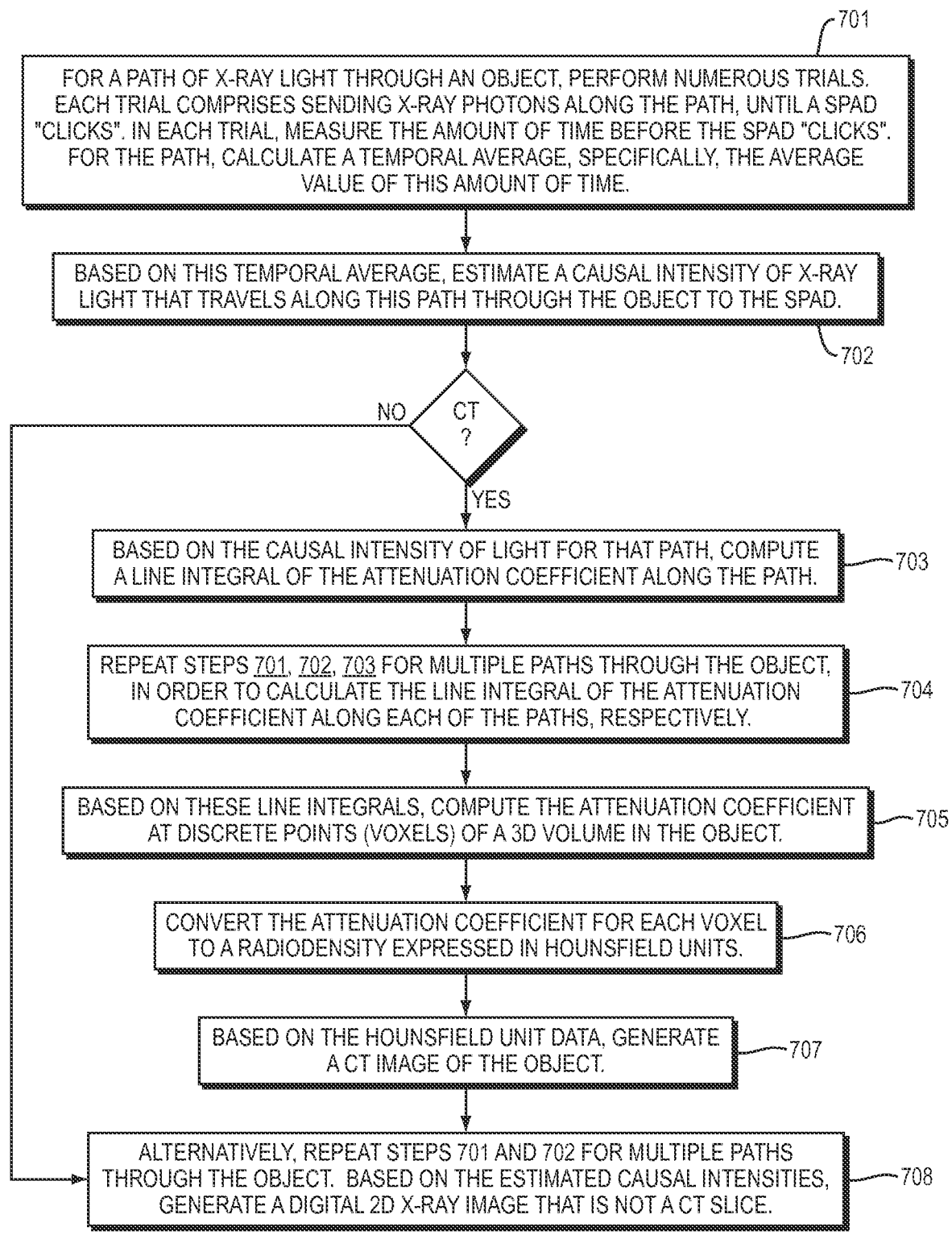
FIG. 7 is a flowchart that shows steps in an imaging method.

FIG. 7 is a flowchart that shows steps in an imaging method, in an illustrative embodiment of this invention. The method shown in FIG. 7 includes the following steps: For a path of X-ray light through an object, perform numerous trials. Each trial comprises sending X-ray photons along the path, until a SPAD "clicks". In each trial, measure the amount of time before the SPAD "clicks". For the path, calculate a temporal average, specifically, the average value of this amount of time (Step 701). Based on this temporal statistic, estimate a causal intensity of X-ray light that travels along this path through the object to the SPAD (Step 702). Based on the causal intensity of light for that path, compute a line integral of the attenuation coefficient along the path (Step 703). Repeat Steps 701, 702, 703 for multiple paths through the object, in order to calculate the line integral of the attenuation coefficient along each of the paths, respectively. (Step 704). Based on these line integrals, compute the attenuation coefficient at discrete points (voxels) of a 3D volume in the object (Step 705). Convert the attenuation coefficient for each voxel to a radiodensity expressed in Hounsfield units (Step 706). Use the Hounsfield unit data to generate a CT image of a slice of the object (Step 707). Alternatively, repeat steps 701 and 702 for multiple paths through the object. Based on the causal intensities, generate a digital 2D X-ray image that is not a CT slice (Step 708).

Figure 8:
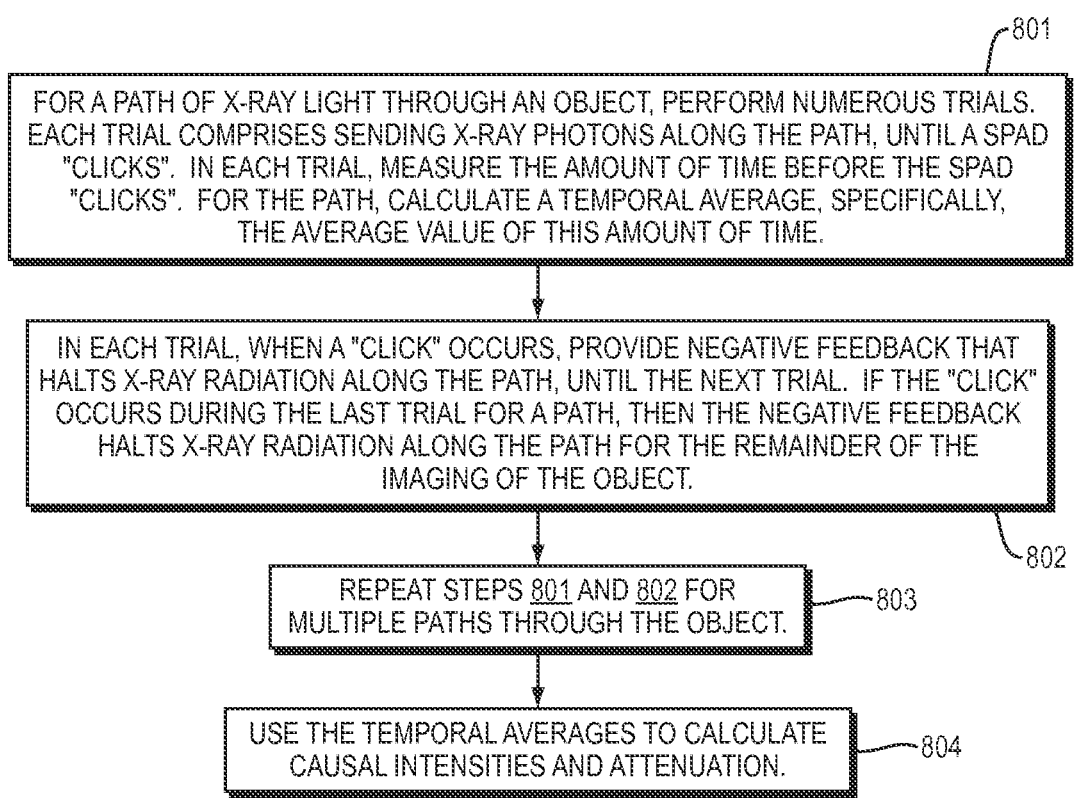
FIG. 8 is a flowchart that shows steps in a method to reduce X-ray dosage during imaging.

FIG. 8 is a flowchart that shows steps in a method to reduce X-ray dosage during imaging, in an illustrative embodiment of this invention. The method shown in FIG. 8 includes the following steps: For a path of X-ray light through an object, perform numerous trials. Each trial comprises sending X-ray photons along the path, until a SPAD "clicks". In each trial, measure the amount of time before the SPAD "clicks". For the path, calculate a temporal average, specifically, the average value of this amount of time (Step 801). In each trial, when a "click" occurs, provide negative feedback that halts X-ray radiation along the path, until the next trial. If the "click" occurs during the last trial for a path, then the negative feedback halts X-ray radiation along the path for the remainder of the imaging of the object (Step 802). Repeat steps 801 and 802 for multiple paths. (Step 803). Use the temporal averages to calculate causal intensities and attenuation (Step 804).

Computers

In exemplary implementations of this invention, one or more electronic computers (e.g. 115, 215, 223, 225, 608, 609) are programmed and specially adapted: (1) to control the operation of, or interface with, hardware components of an X-ray imaging system, including any X-ray source, X-ray sensor, electron multiplier, actuator, I/O device, electronic memory device, power regulator or cooling system; (2) to control a waveform emitted by an X-ray imaging system; (3) to control a light that in turn controls a photocathode, (3) to control a switch that connects/disconnects a field emission cathode to its power supply, (4) to control a power regulator to adjust voltage or current in components of the X-ray imaging system, including to control voltage or current in an X-ray cathode or X-ray cathode, or to control voltage or current in any electrode or magnet for deflecting, accelerating or decelerating electrons in an electron beam; (5) to perform any CT reconstruction algorithm, (6) to calculate Hounsfield units from attenuation coefficients, (7) to calculate a digital 2D X-ray image, including any 2D CT slice image and any 2D image that is not a CT slice, (8) to control an actuator for translating a gantry, (9) to control an actuator for rotating an anode disk, (10) to control a cooling device, including any device for cooling an anode or power regulator, (11) to perform any other calculation, computation, program, algorithm, or computer function described or implied above; (12) to receive signals indicative of human input; (13) to output signals for controlling transducers for outputting information in human perceivable format; and

(14) to process data, to perform computations, to execute any algorithm or software, and to control the read or write of data to and from memory devices (items 1-14 of this sentence referred to herein as the "Computer Tasks"). The one or more computers may be in any position or positions within or outside of the X-ray imaging system. For example, in some cases (a) at least one computer is housed in or together with other components of the X-ray imaging system, such as an X-ray generator, X-ray sensor, gantry or actuator, and (b) at least one computer is remote from other components of the X-ray imaging system. The one or more computers are connected to each other or to other components in the X-ray imaging system either: (a) wirelessly, (b) by wired connection, (c) by fiber-optic link, or (d) by a combination of wired, wireless or fiber optic links.

In exemplary implementations, one or more computers are programmed to perform any and all calculations, computations, programs, algorithms, and computer functions described or implied above. For example, in some cases: (a) a machine-accessible medium has instructions encoded thereon that specify steps in a software program; and (b) the computer accesses the instructions encoded on the machine-accessible medium, in order to determine steps to execute in the program. In exemplary implementations, the machine-accessible medium comprises a tangible non-transitory medium. In some cases, the machine-accessible medium comprises (a) a memory unit or (b) an auxiliary memory storage device. For example, in some cases, a control unit in a computer fetches the instructions from memory.

In illustrative implementations, one or more computers execute programs according to instructions encoded in one or more tangible, non-transitory, computer-readable media. For example, in some cases, these instructions comprise instructions for a computer to perform any calculation, computation, program, algorithm, or computer function described or implied above. For example, in some cases, instructions encoded in a tangible, non-transitory, computer-accessible medium comprise instructions for a computer to perform the Computer Tasks.

Actuators

In illustrative implementations, the X-ray imaging apparatus includes actuators. For example, in some cases, one or more actuators: (a) translate a gantry; (b) translate or rotate a mechanical shutter; or (c) rotate a disk that houses the X-ray anode.

In illustrative implementations, each actuator (including each actuator for actuating any movement) is any kind of actuator, including a linear, rotary, electrical, piezoelectric, electro-active polymer, mechanical or electro-mechanical actuator. In some cases, the actuator includes and is powered by an electrical motor, including any stepper motor or servomotor. In some cases, the actuator includes a gear assembly, drive train, pivot, joint, rod, arm, or other component for transmitting motion. In some cases, one or more sensors are used to detect position, displacement or other data for feedback to one of more of the actuators.

Definitions

The terms "a" and "an", when modifying a noun, do not imply that only one of the noun exists.

To compute "based on" specified information means to perform a computation that takes the specified information as an input.

A "beam" of particles (such as photons or electrons) means a flow of the particles. As used herein, the term "beam" does not imply a shape, rate or direction of the flow.

To say that a single photon avalanche diode "clicks" means that a current induced in or by the diode exceeds the click threshold.

The term "comprise" (and grammatical variations thereof) shall be construed as if followed by "without limitation". If A comprises B, then A includes B and may include other things.

The term "computer" includes any computational device that performs logical and arithmetic operations. For example, in some cases, a "computer" comprises an electronic computational device, such as an integrated circuit, a microprocessor, a mobile computing device, a laptop computer, a tablet computer, a personal computer, or a mainframe computer. In some cases, a "computer" comprises: (a) a central processing unit, (b) an ALU (arithmetic logic unit), (c) a memory unit, and (d) a control unit that controls actions of other components of the computer so that encoded steps of a program are executed in a sequence. In some cases, a "computer" also includes peripheral units including an auxiliary memory storage device (e.g., a disk drive or flash memory), or includes signal processing circuitry. However, a human is not a "computer", as that term is used herein.

"Defined Term" means a term or phrase that is set forth in quotation marks in this Definitions section.

To say that a first variable "depends" on a second variable means the first variable is a function of the second variable. To say that a first variable "depends" at least in part on a second variable means the first variable is a function of at least the second variable and may be a function of other variables also.

To say that a first thing is "due" to a second thing means that the first thing is caused, at least in part, by the second thing.

For an event to occur "during" a time period, it is not necessary that the event occur throughout the entire time period. For example, an event that occurs during only a portion of a given time period occurs "during" the given time period.

The term "e.g." means for example.

The fact that an "example" or multiple examples of something are given does not imply that they are the only instances of that thing. An example (or a group of examples) is merely a non-exhaustive and non-limiting illustration.

"Field emission cathode" means a cathode that emits electrons in the presence of an electrical field such that a majority of the electrons emitted are due to field electron emission and not due to thermally induced flow of electrons from the cathode's surface.

Unless the context clearly indicates otherwise: (1) a phrase that includes "a first" thing and "a second" thing does not imply an order of the two things (or that there are only two of the things); and (2) such a phrase is simply a way of identifying the two things, respectively, so that they each may be referred to later with specificity (e.g., by referring to "the first" thing and "the second" thing later). For example, unless the context clearly indicates otherwise, if an equation has a first term and a second term, then the equation may (or may not) have more than two terms, and the first term may occur before or after the second term in the equation. A phrase that includes a "third" thing, a "fourth" thing and so on shall be construed in like manner.

"For instance" means for example.

To "halt" means to "reduce".

"Herein" means in this document, including text, specification, claims, abstract, and drawings.

As used herein: (1) "implementation" means an implementation of this invention; (2) "embodiment" means an embodiment of this invention; (3) "case" means an implementation of this invention; and (4) "use scenario" means a use scenario of this invention.

The term "include" (and grammatical variations thereof) shall be construed as if followed by "without limitation".

"Intensity" means any measure of or related to intensity, energy or power. For example, the "intensity" of light includes any of the following measures: irradiance, spectral irradiance, radiant energy, radiant flux, spectral power, radiant intensity, spectral intensity, radiance, spectral radiance, radiant exitance, radiant emittance, spectral radiant exitance, spectral radiant emittance, radiosity, radiant exposure or radiant energy density.

"I/O device" means an input/output device. Non-limiting examples of an I/O device include any device for (a) receiving input from a human user, (b) providing output to a human user, or (c) both. Non-limiting examples of an I/O device also include a touch screen, other electronic display screen, keyboard, mouse, microphone, handheld electronic game controller, digital stylus, display screen, speaker, or projector for projecting a visual display.

"Light" means electromagnetic radiation of any frequency. For example, "light" includes, among other things, x-rays, visible light and infrared light. Likewise, any term that directly or indirectly relates to light (e.g., "imaging") shall be construed broadly as applying to electromagnetic radiation of any frequency.

The term "line integral" shall be construed such that, if discrete samples are taken along a path, then the line integral along the path shall mean the sum of the values of the discrete samples.

The term "or" is inclusive, not exclusive. For example A or B is true if A is true, or B is true, or both A or B are true. Also, for example, a calculation of A or B means a calculation of A, or a calculation of B, or a calculation of A and B.

A parenthesis is simply to make text easier to read, by indicating a grouping of words. A parenthesis does not mean that the parenthetical material is optional or may be ignored.

"Causal intensity" means an intensity of light, which intensity is estimated based on an average of temporal measurements. A non-limiting example of "causal intensity" is a relative intensity of X-ray light that is estimated based on an average of temporal measurements.

A "pulse" of a rectangular waveform means a portion of the period of the waveform, during which portion the waveform is in an active or high state. For example, if the duty cycle of a rectangular waveform is 10%, then a pulse occurs during only 10% of each period of the rectangular waveform.

"Relative intensity" means an intensity that is proportional to actual intensity.

As used herein, the term "set" does not include a group with no elements. Mentioning a first set and a second set does not, in and of itself, create any implication regarding whether or not the first and second sets overlap (that is, intersect).

"Single-avalanche photodiode" (also called a "SPAD") means an avalanche photodiode that is reverse biased above breakdown voltage.

"Single-photon detector" means a sensor that maps incident photon energy to a thresholded state measurement (e.g., as implemented through the use of a comparator).

A "single-photon sensor" means: (a) a single photon avalanche diode; (b) a superconducting nanowire single-photon detector; (c) a photomultiplier tube; or (d) a CdTe direct detection sensor.

Some" means one or more.

As used herein, a "subset" of a set consists of less than all of the elements of the set.

"Substantially" means at least ten percent. For example: (a) 112 is substantially larger than 100; and (b) 108 is not substantially larger than 100.

The term "such as" means for example.

"Temporal measurement" means a measurement of time duration.

"Thermionic emission" means a thermally induced flow of charge carriers from a surface or over a potential-energy barrier. For example, the charge carriers may comprise electrons and the surface may comprise a surface of a cathode.

To say that a machine-readable medium is "transitory" means that the medium is a transitory signal, such as an electromagnetic wave.

"Timer" means a computer or circuit that is programmed or hardwired to measure time with respect to a reference clock.

"Trial" means a trial, as that term is used in the academic field of probability.

"Voxel" means a discrete spatial point.

"X-ray source" means an apparatus that emits X-rays, including any anode of the apparatus and any cathode that emits electrons that impact the anode.

Except to the extent that the context clearly requires otherwise, if steps in a method are described herein, then the method includes variations in which: (1) steps in the method occur in any order or sequence, including any order or sequence different than that described; (2) any step or steps in the method occurs more than once; (3) different steps, out of the steps in the method, occur a different number of times during the method, (4) any combination of steps in the method is done in parallel or serially; (5) any step or steps in the method is performed iteratively; (6) a given step in the method is applied to the same thing each time that the given step occurs or is applied to different things each time that the given step occurs; or (7) the method includes other steps, in addition to the steps described.

This Definitions section shall, in all cases, control over and override any other definition of the Defined Terms. For example, the definitions of Defined Terms set forth in this Definitions section override common usage or any external dictionary. If a given term is explicitly or implicitly defined in this document, then that definition shall be controlling, and shall override any definition of the given term arising from any source (e.g., a dictionary or common usage) that is external to this document. If this document provides clarification regarding the meaning of a particular term, then that clarification shall, to the extent applicable, override any definition of the given term arising from any source (e.g., a dictionary or common usage) that is external to this document. To the extent that any term or phrase is defined or clarified herein, such definition or clarification applies to any grammatical variation of such term or phrase, taking into account the difference in grammatical form. For example, the grammatical variations include noun, verb, participle, adjective, and possessive forms, and different declensions, and different tenses. In each case described in this paragraph, the Applicant or Applicants are acting as his, her, its or their own lexicographer.

Variations

This invention may be implemented in many different ways. Here are some non-limiting examples:

This invention is not limited to imaging biological tissue. Instead, this invention may be used to image any material. In use scenarios where biological tissue is not being imaged, the "tissue" that is being imaged is replaced with an "object" being imaged.

In one aspect, this invention is a method comprising, in combination: (a) an X-ray source emitting, in repeated trials, X-ray photons along a path that intersects an object; (b) in each respective trial, out of the repeated trials (i) a sensor detecting an event, which event is stochastic and is due to at least some of photons passing through the object and reaching the sensor, and (ii) a timer measuring a temporal duration, which temporal duration is stochastic and depends, at least in part, on when the event occurs during the respective trial; and (c) one or more computers (i) calculating a temporal average, which temporal average is an average of temporal durations measured by the timer in the repeated trials, and (ii) calculating, based on the temporal average, a causal intensity, which causal intensity is an estimate of intensity of X-ray light that passes through the object along the path and reaches the sensor. In some cases, the one or more computers calculate, based on the causal intensity, a line integral of an attenuation coefficient along the path. In some cases, the steps described in the preceding two sentences are repeated for multiple paths, such that the one or more computers calculate a set of line integrals of an attenuation coefficient, which set includes a line integral for each of the multiple paths, respectively. In some cases, the one or more computers calculate, based on the set of line integrals, a set of attenuation coefficients, which set of attenuation coefficients includes an attenuation coefficient for each voxel, respectively, in a set of voxels in the object. In some cases, the one or more computers: (a) convert the set of attenuation values into a set of radiodensity values, which radiodensity values are expressed in Hounsfield units; and (b) calculate a computed tomography image. In some cases, steps (a), (b) and (c) of the first sentence of this paragraph are repeated for a plurality of paths, such that the one or more computers calculate a set of causal intensities, which set of causal intensities includes a causal intensity for each respective path out of the plurality of paths. In some cases, the one or more computers calculate, based on the set of causal intensities, a 2D digital X-ray image. In some cases, the 2D digital X-ray image is not a computed tomography image. In some cases, the intensity of X-ray light is a relative intensity. In some cases, the sensor is single-photon avalanche diode and the event is an avalanche current. In some cases, the sensor is a single-photon detector. In some cases, in each respective trial out of the multiple trials, detection by the sensor of the event triggers negative feedback that causes the X-ray source to halt, at least temporarily, the emitting of X-ray photons. In some cases: (a) the X-ray source includes a photocathode; and (b) the halt is due to turning off a light source that, prior to being turned off, illuminates the photocathode. In some cases: (a) the X-ray source includes a field emission cathode; and (b) the halt is due to electrically disconnecting the field emission cathode from a power source, such that current ceases, at least temporarily, to flow through the field emission cathode. In some cases, the halt is due to moving a mechanical shutter to a spatial position such that the mechanical shutter blocks X-ray photons emitted by the X-ray source from reaching the object. In some cases, the halt is due to moving a given shutter to a spatial position such that electrons impact the given shutter, which electrons are emitted by a cathode of the X-ray source. In some cases, the halt is due, at least in part, to one or more electrodes creating an electric field that deflects electrons emitted by a cathode of the X-ray source. In some cases, the halt is due, at least in part, to one or more magnets creating a magnetic field that deflects electrons emitted by a cathode of the X-ray source. In some cases, the halt is due, at least in part, to one or more electrodes creating an electric field that reduces the speed of electrons emitted by a cathode of the X-ray source. In some cases, the halt is due, at least in part, to one or more magnets creating a magnetic field that reduces the speed of electrons emitted by a cathode of the X-ray source. In some cases, when the event occurs depends, at least in part, on the actual intensity of light passing through the object along the path and reaching the sensor. In some cases, the sensor is a single-photon sensor. In some cases, the causal intensity is an estimate of actual intensity of X-ray light that passes through the object along the path and reaches the sensor. In some cases, the causal intensity is an estimate of relative intensity of X-ray light that passes through the object along the path and reaches the sensor. Each of the cases described above in this paragraph is an example of the method described in the first sentence of this paragraph, and is also an example of an embodiment of this invention that may be combined with other embodiments of this invention.

In another aspect, this invention is an apparatus comprising, in combination: (a) an X-ray source for emitting, in repeated trials, X-ray photons along a path that intersects an object; (b) a sensor for detecting, in each of the repeated trials, an event that is stochastic and is due to at least some of photons passing through the object and reaching the sensor; (c) a timer for measuring, in each respective trial out of the repeated trials, a temporal duration, which temporal duration is stochastic and depends, at least in part, on when the event occurs during the respective trial; and (d) one or more computers that are programmed (i) to calculate a temporal average, which temporal average is an average of temporal durations measured by the timer in the repeated trials, and (ii) to calculate, based on the temporal average, a causal intensity, which causal intensity is an estimate of intensity of X-ray light that passes through the object along the path and reaches the sensor. In some cases, the one or more computers are programmed to calculate, based on the causal intensity, a line integral of an attenuation coefficient along the path. In some cases, the one or more computers are programmed to calculate a set of line integrals of an attenuation coefficient, which set includes a line integral for each path in a set of multiple paths, respectively. In some cases, the one or more computers are programmed to calculate, based on the set of line integrals, a set of attenuation coefficients, which set of attenuation coefficients includes an attenuation coefficient for each voxel, respectively, in a set of voxels in the object. In some cases, the one or more computers are programmed to: (a) convert the set of attenuation values into a set of radiodensity values, which radiodensity values are expressed in Hounsfield units; and (b) calculate a computed tomography image. In some cases, the one or more computers are programmed to calculate a set of causal intensities, which set of causal intensities includes a causal intensity for each respective path out of a plurality of paths. In some cases, the one or more computers are programmed to calculate, based on the set of causal intensities, a 2D digital X-ray image. In some cases, the 2D digital X-ray image is not a computed tomography image. In some cases, the intensity of X-ray light is a relative intensity.

In some cases, the sensor is single-photon avalanche diode and the event is an avalanche current. In some cases, the sensor is a single-photon detector. In some cases, the one or more computers are programmed such that detection by the sensor of the event triggers the one or more computers to provide negative feedback that causes the X-ray source to halt, at least temporarily, the emitting of X-ray photons. In some cases: (a) the X-ray source includes a photocathode; and (b) the halt is due to turning off a light source that, prior to being turned off, illuminates the photocathode. In some cases: (a) the X-ray source includes a field emission cathode; and (b) the halt is due to electrically disconnecting the field emission cathode from a power source, such that current ceases, at least temporarily, to flow through the field emission cathode. In some cases, the halt is due to moving a mechanical shutter to a spatial position such that the mechanical shutter blocks X-ray photons emitted by the X-ray source from reaching the object. the halt is due to moving a given shutter to a spatial position such that electrons impact the given shutter, which electrons are emitted by a cathode of the X-ray source. In some cases, the halt is due, at least in part, to one or more electrodes creating an electric field that deflects electrons emitted by a cathode of the X-ray source. In some cases, the halt is due, at least in part, to one or more magnets creating a magnetic field that deflects electrons emitted by a cathode of the X-ray source. In some cases, the halt is due, at least in part, to one or more electrodes creating an electric field that reduces the speed of electrons emitted by a cathode of the X-ray source. In some cases, the halt is due, at least in part, to one or more magnets creating a magnetic field that reduces the speed of electrons emitted by a cathode of the X-ray source. In some cases, when the event occurs depends, at least in part, on the actual intensity of light passing through the object along the path and reaching the sensor. In some cases, the sensor is a single-photon sensor. In some cases, the causal intensity is an estimate of actual intensity of X-ray light that passes through the object along the path and reaches the sensor. In some cases, the causal intensity is an estimate of relative intensity of X-ray light that passes through the object along the path and reaches the sensor. Each of the cases described above in this paragraph is an example of the apparatus described in the first sentence of this paragraph, and is also an example of an embodiment of this invention that may be combined with other embodiments of this invention.

In another aspect, this invention is a method comprising, in combination: (a) an X-ray source emitting, in repeated trials, X-ray photons along a path that intersects an object; (b) in each respective trial, out of the repeated trials (i) a sensor detecting an event, which event is stochastic and is due to at least some of photons passing through the object and reaching the sensor, and (ii) a timer measuring a temporal duration, which temporal duration is stochastic and depends, at least in part, on when the event occurs during the respective trial; and (c) one or more computers calculating a temporal average, which temporal average is an average of temporal durations measured by the timer in the repeated trials; wherein detection by the sensor of the event triggers negative feedback that causes the X-ray source to halt, at least temporarily, the emitting of X-ray photons. the sensor is single-photon avalanche diode and the event is an avalanche current. In some cases, the sensor is a single-photon detector. In some cases: (a) the X-ray source includes a photocathode; and (b) the halt is due to turning off a light source that, prior to being turned off, illuminates the photocathode. In some cases: (a) the X-ray source includes a field emission cathode; and (b) the halt is due to electrically disconnecting the field emission cathode from a power source, such that current ceases, at least temporarily, to flow through the field emission cathode. In some cases, the halt is due to moving a mechanical shutter to a spatial position such that the mechanical shutter blocks X-ray photons emitted by the X-ray source from reaching the object. In some cases, the halt is due to moving a given shutter to a spatial position such that electrons impact the given shutter, which electrons are emitted by a cathode of the X-ray source. In some cases, the halt is due, at least in part, to one or more electrodes creating an electric field that deflects electrons emitted by a cathode of the X-ray source. In some cases, the halt is due, at least in part, to one or more magnets creating a magnetic field that deflects electrons emitted by a cathode of the X-ray source. In some cases, the halt is due, at least in part, to one or more electrodes creating an electric field that reduces the speed of electrons emitted by a cathode of the X-ray source. In some cases, the halt is due, at least in part, to one or more magnets creating a magnetic field that reduces the speed of electrons emitted by a cathode of the X-ray source. Each of the cases described above in this paragraph is an example of the method described in the first sentence of this paragraph, and is also an example of an embodiment of this invention that may be combined with other embodiments of this invention.

In another aspect, this invention is an apparatus comprising, in combination: (a) an X-ray source for emitting, in repeated trials, X-ray photons along a path that intersects an object; (b) a sensor for detecting, in each of the repeated trials, an event that is stochastic and is due to at least some of photons passing through the object and reaching the sensor; (c) a timer for measuring, in each respective trial out of the repeated trials, a temporal duration, which temporal duration is stochastic and depends, at least in part, on when the event occurs during the respective trial; and (d) one or more computers that are programmed to calculate a temporal average, which temporal average is an average of temporal durations measured by the timer in the repeated trials; wherein the one or more computers are programmed such that detection by the sensor of the event triggers the one or more computers to provide negative feedback that causes the X-ray source to halt, at least temporarily, the emitting of X-ray photons. In some cases, the sensor is single-photon avalanche diode and the event is an avalanche current. In some cases, the sensor is a single-photon detector. In some cases: (a) the X-ray source includes a photocathode; and (b) the halt is due to turning off a light source that, prior to being turned off, illuminates the photocathode. In some cases: (a) the X-ray source includes a field emission cathode; and (b) the halt is due to electrically disconnecting the field emission cathode from a power source, such that current ceases, at least temporarily, to flow through the field emission cathode. In some cases, the halt is due to moving a mechanical shutter to a spatial position such that the mechanical shutter blocks X-ray photons emitted by the X-ray source from reaching the object. In some cases, the halt is due to moving a given shutter to a spatial position such that electrons impact the given shutter, which electrons are emitted by a cathode of the X-ray source. In some cases, the halt is due, at least in part, to one or more electrodes creating an electric field that deflects electrons emitted by a cathode of the X-ray source. In some cases, the halt is due, at least in part, to one or more magnets creating a magnetic field that deflects electrons emitted by a cathode of the X-ray source. In some cases, the halt is due, at least in part, to one or more electrodes creating an electric field that reduces the speed of electrons emitted by a cathode of the X-ray source. In some cases, the halt is due, at least in part, to one or more magnets creating a magnetic field that reduces the speed of electrons emitted by a cathode of the X-ray source. Each of the cases described above in this paragraph is an example of the apparatus described in the first sentence of this paragraph, and is also an example of an embodiment of this invention that may be combined with other embodiments of this invention.

The above description (including without limitation any attached drawings and figures) describes illustrative implementations of the invention. However, the invention may be implemented in other ways. The methods and apparatus which are described above are merely illustrative applications of the principles of the invention. Other arrangements, methods, modifications, and substitutions by one of ordinary skill in the art are therefore also within the scope of the present invention. Numerous modifications may be made by those skilled in the art without departing from the scope of the invention. Also, this invention includes without limitation each combination and permutation of one or more of the abovementioned implementations, embodiments and features.

What is claimed is:

1. A method comprising:
   (a) estimating a set of causal intensities for a set of multiple paths, which paths intersect a region of a physical object; and
   (b) calculating, based on the set of causal intensities, a computed tomography image of the region of the physical object
   wherein each specific causal intensity in the set of causal intensities is calculated for a specific path in the set of multiple paths, by steps that include
   (i) emitting, in repeated trials, X-ray photons that travel along the specific path,
   (ii) in each particular trial, out of the repeated trials
   (A) detecting an event, which event is stochastic and is due to at least some of photons passing through the object along the specific path and reaching a sensor, and
   (B) measuring a temporal duration, which temporal duration is stochastic and depends, at least in part, on when the event occurs during the particular trial,
   (iii) calculating a temporal average, which temporal average is an average of temporal durations measured in the repeated trials for the specific path, and
   (iv) calculating, based on the temporal average, the specific causal intensity, which specific causal intensity is an estimate of intensity of X-ray light that passes through the object along the specific path and reaches the sensor.

2. The method of claim 1, wherein the object comprises tissue.

3. The method of claim 1, wherein detection by the sensor of the event triggers negative feedback that causes an X-ray source to halt, at least temporarily, the emitting of X-ray photons.

4. The method of claim 3, wherein:
   (a) the X-ray source includes a photocathode; and
   (b) the halt is due to turning off a light source that, prior to being turned off, illuminates the photocathode.

5. The method of claim 3, wherein:
   (a) the X-ray source includes a field emission cathode; and
   (b) the halt is due to electrically disconnecting the field emission cathode from a power source, in such a way that current ceases, at least temporarily, to flow through the field emission cathode.

6. The method of claim 3, wherein the halt is due, at least in part, to one or more electrodes creating an electric field that deflects electrons emitted by a cathode of the X-ray source.

7. The method of claim 3, wherein the halt is due, at least in part, to one or more magnets creating a magnetic field that deflects electrons emitted by a cathode of the X-ray source.

8. The method of claim 3, wherein the halt is due, at least in part, to one or more electrodes creating an electric field that reduces the speed of electrons emitted by a cathode of the X-ray source.

9. The method of claim 3, wherein the halt is due, at least in part, to one or more magnets creating a magnetic field that reduces the speed of electrons emitted by a cathode of the X-ray source.

10. A method comprising:
    (a) emitting, in repeated trials, X-ray photons along a path that intersects an object;
    (b) in each particular trial, out of the repeated trials
       (i) detecting an event that is stochastic and is due to at least some of photons passing through the object and reaching a sensor, and
       (ii) measuring a temporal duration, which temporal duration is stochastic and depends, at least in part, on when the event occurs during the particular trial;
    (c) calculating a temporal average, which temporal average is an average of temporal durations measured in the repeated trials;
    (d) calculating, based on the temporal average, a causal intensity, which causal intensity is an estimate of intensity of X-ray light that passes through the object along the path and reaches the sensor;
    (e) calculating, based on the causal intensity, a line integral of an attenuation coefficient along the path;
    (f) repeating, each time for a different path, the sequence of steps described in clauses (a), (b), (c), (d) and (e) of this claim, until the sequence of steps has been performed for multiple paths and a set of line integrals has been calculated, which set of line integrals includes a line integral for each of the multiple paths;
    (g) calculating, based on the set of line integrals, a set of attenuation coefficients, which set of attenuation coefficients includes an attenuation coefficient for each voxel in a set of voxels in the object
    (h) converting the set of attenuation coefficients into a set of radiodensity values; and
    (i) calculating, based on the radiodensity values, a computed tomography image.

11. An apparatus comprising:
    (a) an X-ray source;
    (b) a sensor;
    (c) a timer; and
    (d) one or more computers;
    wherein
       (i) the apparatus is configured to take measurements of a set of causal intensities for a set of multiple paths, which paths intersect a region of a physical object,
       (ii) the apparatus is configured to take the measurements in such a way that a specific causal intensity in the set of causal intensities is estimated for each specific path in the set of multiple paths, by steps that include
          (A) the X-ray source emitting, in repeated trials, X-ray photons that travel along the specific path,
          (B) in each particular trial, out of the repeated trials
             (I) the sensor detecting an event, which event is stochastic and is due to at least some of photons passing through the object along the specific path and reaching the sensor, and (II) the timer measuring a temporal duration, which temporal duration is stochastic and depends, at least in part, on when the event occurs during the particular trial, and (C) the one or more computers (I) calculating a temporal average, which temporal average is an average of temporal durations measured by the timer in the repeated trials for the specific path, and (II) calculating, based on the temporal average, the specific causal intensity, which specific causal intensity is an estimate of intensity of X-ray light that passes through the object along the specific path and reaches the sensor, and (iii) the one or more computers are programmed to calculate, based on the set of causal intensities, a computed tomography image of the region of the physical object.

12. The apparatus of claim 11, wherein the object comprises tissue.

13. The apparatus of claim 11, wherein the sensor is a single-photon avalanche diode and the event is an avalanche current.

14. The apparatus of claim 11, wherein, the one or more computers are programmed in such a way that detection by the sensor of the event triggers the one or more computers to output instructions that cause the X-ray source to halt, at least temporarily, the emitting of X-ray photons.

15. A method comprising:
(a) estimating a set of causal intensities for a set of multiple paths, which paths intersect a region of a physical object; and
(b) calculating, based on the set of causal intensities, a digital radiographic image of the region of the physical object;
wherein each specific causal intensity in the set of causal intensities is calculated for a specific path in the set of multiple paths, by steps that include
(i) emitting, in repeated trials, X-ray photons that travel along the specific path,
(ii) in each particular trial, out of the repeated trials
(A) detecting an event, which event is stochastic and is due to at least some of photons passing through the object along the specific path and reaching a sensor, and
(B) measuring a temporal duration, which temporal duration is stochastic and depends, at least in part, on when the event occurs during the particular trial,
(iii) calculating a temporal average, which temporal average is an average of temporal durations measured in the repeated trials for the specific path, and
(iv) calculating, based on the temporal average, the specific causal intensity, which specific causal intensity is an estimate of intensity of X-ray light that passes through the object along the specific path and reaches the sensor.

16. The method of claim 15, wherein detection by the sensor of the event triggers negative feedback that causes an X-ray source to halt, at least temporarily, the emitting of X-ray photons.

17. The method of claim 16, wherein:
(a) the X-ray source includes a photocathode; and
(b) the halt is due to turning off a light source that, prior to being turned off, illuminates the photocathode.

18. The method of claim 16, wherein:
(a) the X-ray source includes a field emission cathode; and
(b) the halt is due to electrically disconnecting the field emission cathode from a power source, in such a way that current ceases, at least temporarily, to flow through the field emission cathode.

19. An apparatus comprising:
(a) an X-ray source;
(b) a sensor;
(c) a timer; and
(d) one or more computers;
wherein
(i) the apparatus is configured to take measurements of a set of causal intensities for a set of multiple paths, which paths intersect a region of a physical object,
(ii) the apparatus is configured to take the measurements in such a way that a specific causal intensity in the set of causal intensities is estimated for each specific path in the set of multiple paths, by steps that include
(A) the X-ray source emitting, in repeated trials, X-ray photons that travel along the specific path,
(B) in each particular trial, out of the repeated trials
(I) the sensor detecting an event, which event is stochastic and is due to at least some of photons passing through the object along the specific path and reaching the sensor, and
(II) the timer measuring a temporal duration, which temporal duration is stochastic and depends, at least in part, on when the event occurs during the particular trial, and
(C) the one or more computers
(I) calculating a temporal average, which temporal average is an average of temporal durations measured by the timer in the repeated trials for the specific path, and
(II) calculating, based on the temporal average, the specific causal intensity, which specific causal intensity is an estimate of intensity of X-ray light that passes through the object along the specific path and reaches the sensor, and
(iii) the one or more computers are programmed to calculate, based on the set of causal intensities, a digital radiographic image of the region of the physical object.

20. The apparatus of claim 19, wherein, the one or more computers are programmed in such a way that detection by the sensor of the event triggers the one or more computers to output instructions that cause the X-ray source to halt, at least temporarily, the emitting of X-ray photons.

* * * * *